(12) United States Patent
Lee

(10) Patent No.: US 10,405,949 B2
(45) Date of Patent: Sep. 10, 2019

(54) METHODS AND DEVICES FOR APPLYING ORTHODONTIC BRACKETS

(71) Applicant: Daniel Lee, San Jose, CA (US)

(72) Inventor: Daniel Lee, San Jose, CA (US)

(*) Notice: Subject to any disclaimer, the term of this patent is extended or adjusted under 35 U.S.C. 154(b) by 0 days.

(21) Appl. No.: 15/587,061

(22) Filed: May 4, 2017

(65) Prior Publication Data
US 2018/0318046 A1 Nov. 8, 2018

(51) Int. Cl.
A61C 7/14 (2006.01)
A61C 7/16 (2006.01)
A61C 7/00 (2006.01)

(52) U.S. Cl.
CPC .............. A61C 7/146 (2013.01); A61C 7/002 (2013.01); A61C 7/16 (2013.01)

(58) Field of Classification Search
CPC ........... A61C 7/146; A61C 7/16; A61C 7/002; A44C 15/007
USPC ..................................... 433/3, 8–24
See application file for complete search history.

(56) References Cited

U.S. PATENT DOCUMENTS

| 5,158,452 | A | | 10/1992 | Franseen et al. | |
|---|---|---|---|---|---|
| 5,454,717 | A | * | 10/1995 | Andreiko | A61C 7/00 433/24 |
| 5,863,198 | A | * | 1/1999 | Doyle | A61C 7/146 433/3 |
| 7,131,836 | B1 | | 11/2006 | Kesling | |
| 8,550,815 | B2 | | 10/2013 | Sachdeva | |
| 2002/0028417 | A1 | * | 3/2002 | Chapoulaud | A61C 7/00 433/24 |
| 2002/0086263 | A1 | * | 7/2002 | Kyung | A61C 7/146 433/72 |
| 2005/0003320 | A1 | | 1/2005 | Freeman, Jr. et al. | |
| 2005/0074716 | A1 | * | 4/2005 | Cleary | A61C 7/146 433/3 |
| 2007/0254257 | A1 | * | 11/2007 | Sachdeva | A61C 7/146 433/9 |

(Continued)

FOREIGN PATENT DOCUMENTS

| CN | 2461504 Y | 11/2001 |
|---|---|---|
| KR | 10-1685606 B1 | 12/2016 |
| WO | WO2005/039433 A1 | 5/2005 |

OTHER PUBLICATIONS

Grauer, Computer-Aided Design/computer-Aided Manufacturing Technology in Customized Orthodontic Appliances, © 2012 Willey Periodicals, Inc., Journal of Esthetic and Restorative Dentistry, vol. 24, No. 1, 2012, 7 pgs.

(Continued)

Primary Examiner — Matthew M Nelson
(74) Attorney, Agent, or Firm — Morgan, Lewis & Bockius LLP

(57) ABSTRACT

The various embodiments described herein include a method for applying a set of orthodontic brackets to a set of teeth of a patient. The method includes: (1) for each tooth in the set of teeth, determining an optimal orientation for a respective orthodontic bracket in the set of orthodontic brackets to be mounted to the tooth; (2) producing a bracket applicator configured to mount each orthodontic bracket in the set of orthodontic brackets to the respective tooth in the set of teeth in the respective optimal orientation; and (3) mounting the set of orthodontic brackets to the set of teeth using the bracket applicator and a bonding material.

18 Claims, 30 Drawing Sheets

(56) References Cited

U.S. PATENT DOCUMENTS

| | | | |
|---|---|---|---|
| 2008/0020338 A1 | 1/2008 | Zakhem et al. | |
| 2008/0233531 A1* | 9/2008 | Raby ........................ | A61C 7/02 433/24 |
| 2010/0216083 A1 | 8/2010 | Grobbee | |
| 2012/0094245 A1* | 4/2012 | Kuperman ............. | A61C 7/146 433/3 |
| 2012/0251969 A1* | 10/2012 | Reising .................. | A61C 7/145 433/3 |
| 2014/0287376 A1 | 9/2014 | Hultgren et al. | |
| 2015/0050612 A1 | 2/2015 | Damon et al. | |
| 2016/0000526 A1 | 1/2016 | Tam et al. | |
| 2016/0000529 A1* | 1/2016 | Kim ........................ | A61C 7/002 433/3 |
| 2016/0051342 A1* | 2/2016 | Phan ....................... | A61C 7/146 702/150 |
| 2016/0228214 A1* | 8/2016 | Sachdeva ............... | A61C 7/002 |

OTHER PUBLICATIONS

Lee, International Search Report and Written Opinion dated Apr. 16, 2018, received in PCT/US2018/027725, which corresponds to U.S. Appl. No. 15/587,061, 12 pgs. (Lee).

* cited by examiner

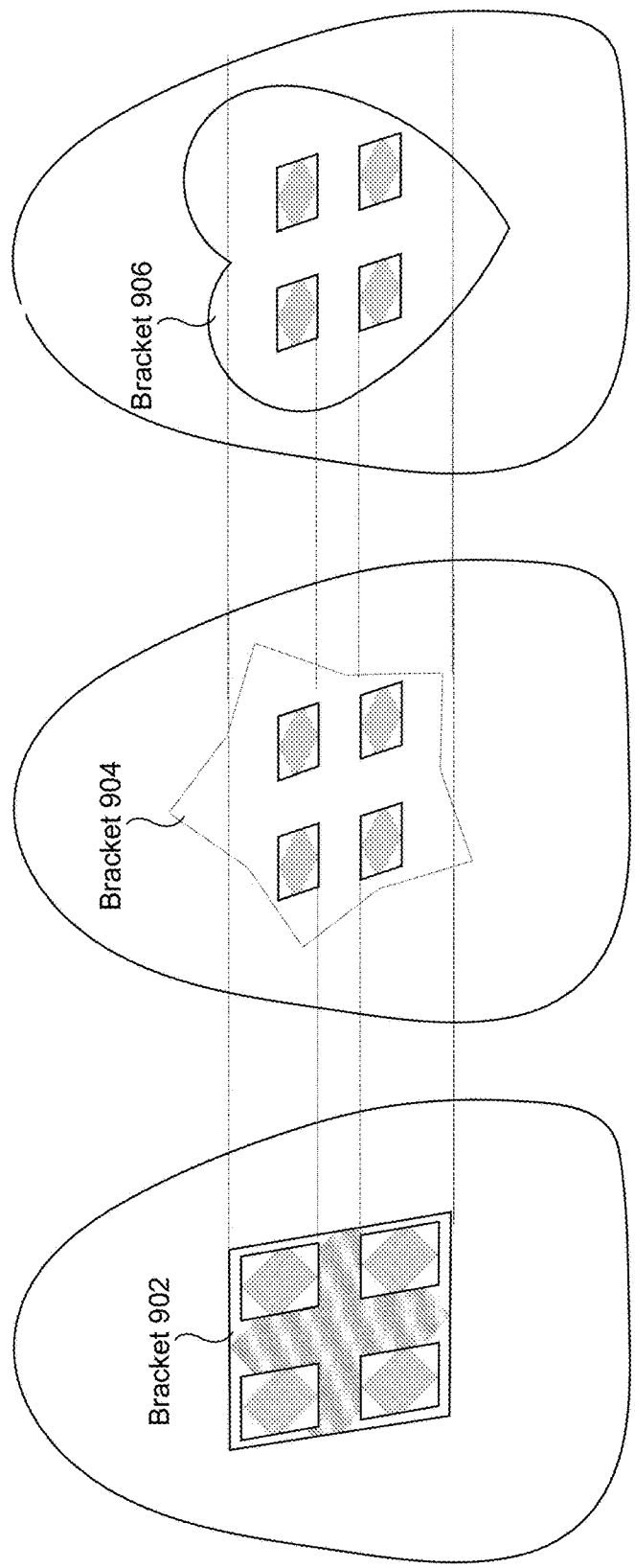

METHODS AND DEVICES FOR APPLYING ORTHODONTIC BRACKETS

TECHNICAL FIELD

The disclosed implementations relates generally to applying orthodontic brackets, including but not limited, to producing a bracket applicator for mounting a set of orthodontic brackets.

BACKGROUND

There continues to be an increase in demand for orthodontics to diagnosis, prevent, and/or correct malpositioned teeth and jaws. One of the primary methods for correcting malpositioned teeth and jaws is the application of orthodontic brackets (also sometimes called braces) to a patient's teeth. Each orthodontic bracket is affixed to a tooth and wires and/or bands connecting the brackets are used to realign the patient's teeth and/or jaws.

The orthodontic brackets are typically manufactured in bulk and include a handful of preset design options. These pre-manufactured orthodontic brackets are not designed so as to precisely fit the patient's individual teeth nor are they designed to correct the patient's particular malpositioning. Thus, an orthodontist will generally survey a patient's teeth and select a preset design option that either most closely fits the patient's teeth or is most suitable for the correction mechanism the orthodontist wishes to apply. However, the use of non-personalized orthodontic brackets leads to non-optimal results, where individual teeth cannot be precisely realigned. For example, with non-personalized orthodontic brackets the amount of force applied to particular teeth can be either insufficient to properly realign the teeth resulting in delays or failure; or unnecessarily high causing unnecessary pain to a patient and potentially damaging the teeth.

Moreover, the non-personalized orthodontic brackets are difficult to affix to the teeth with the accurate and precise positioning needed to optimize correction of malpositioned teeth and jaws. In addition, the non-personalized orthodontic brackets can also become detached from the teeth because they weren't precisely affixed.

SUMMARY

Accordingly, there is a need for new devices and methods for applying orthodontic brackets in a manner that is optimized to individual patients. Such methods optionally complement or replace conventional methods for applying orthodontic brackets. The various implementations described herein include systems, methods, and devices used to apply orthodontic brackets.

(A1) In one aspect, some implementations include a method for applying a set of orthodontic brackets to a set of teeth of a patient. The method includes: (i) for each tooth in the set of teeth, determining an optimal orientation for a respective orthodontic bracket in the set of orthodontic brackets to be mounted to the tooth; (ii) producing a bracket applicator configured to mount each orthodontic bracket in the set of orthodontic brackets to the respective tooth in the set of teeth in the respective optimal orientation; and (iii) mounting the set of orthodontic brackets to the set of teeth using the bracket applicator and a bonding material. In some implementations, the bonding material comprises a resin.

(A2) In some implementations of the method of A1, determining the optimal orientation includes determining an optimal tip, torque, and/or rotation for the respective orthodontic bracket.

(A3) In some implementations of the method of any one of A1-A2, determining the optimal orientation comprises utilizing a 3-dimensional model of the set of teeth to determine the optimal orientation.

(A4) In some implementations of the method of any one of A1-A3, the respective optimal orientation for a first orthodontic bracket is distinct from the respective optimal orientation for a second orthodontic bracket.

(A5) In some implementations of the method of any one of A1-A4, the bracket applicator is configured to utilize one or more respective tooth surfaces to position each orthodontic bracket at the respective optimal orientation. In some implementations, the incisal edge of the tooth is used as a vertical stop. In some implementations, the bracket applicator includes three anchor points configured to removably couple to the tooth.

(A6) In some implementations of the method of any one of A1-A5: (i) the method further includes producing a mold of the set of teeth of the patient; and (ii) producing the bracket applicator includes producing the bracket applicator based on the mold and the respective optimal orientations.

(A7) In some implementations of the method of any one of A1-A6, the bracket applicator includes a plurality of tooth mounts and a connector coupling the plurality of tooth mounts to one another.

(B1) In another aspect, some implementations include a bracket applicator for applying a set of orthodontic brackets to a set of teeth of a patient. The bracket applicator includes: (i) a bracket mount configured to secure an orthodontic bracket; and (ii) a tooth mount coupled to the bracket mount, the tooth mount configured to mount the orthodontic bracket to a tooth in a particular orientation.

(B2) In some implementations of the bracket applicator of B1, the bracket applicator further includes: (i) a plurality of additional bracket mounts each configured to secure a respective orthodontic bracket; (ii) a plurality of additional tooth mounts coupled to the plurality of additional bracket mounts; and (iii) a connector coupling the tooth mount to each tooth mount in the plurality of additional tooth mounts, the connector configured to enable concurrent mounting of each orthodontic bracket at a respective particular orientation.

(B3) In some implementations of the bracket applicator of B2, the bracket applicator further includes a handle section configured to provide rigidity to the tooth mount and the plurality of additional tooth mounts during mounting. In some implementations, the handle comprises a squeeze handle configured such that squeezing the handle facilitates insertion/removal of the bracket applicator into the patient's mount and releasing the squeeze applies pressure between the tooth mounts and the teeth to facilitate bonding.

(B4) In some implementations of the bracket applicator of any one of B2-B3: (i) the connector includes a plurality of connecting sections, each connecting section of the plurality of connecting sections coupling two adjacent tooth mounts; and (ii) at least one connecting section of the plurality of connecting sections is distinct from at least one other connecting section of the plurality of connecting sections.

(B5) In some implementations of the bracket applicator of any one of B2-B4, the connector is coupled to the tooth mount and each tooth mount of the plurality of additional tooth mounts via a respective connector fastener. In some implementations, the connector fasteners comprise screws or pins.

(B6) In some implementations of the bracket applicator of any one of B1-B5, the bracket mount is further configured to enable removal of excess bonding material during mounting of the orthodontic bracket. In some implementations, removal of the excess bonding material includes draining off the excess bonding material via an exit vent. In some implementations, the exit vent is on an occlusal side or a gingival side of the tooth.

(B7) In some implementations of the bracket applicator of any one of B1-B6, the bracket mount is further configured to minimize bonding of the bracket mount to a tooth. In some implementations, the bracket mount is configured such that it has a positive release angle. In some implementations, the bracket mount is configured such that it minimizes surface area in contact with the tooth during the mounting process.

(B8) In some implementations of the bracket applicator of any one of B1-B7, the bracket mount is further configured to selectively release the orthodontic bracket without weakening a bond between the orthodontic bracket and a tooth. In some implementations, the bracket mount is configured such that the bracket can be removed by applying simultaneous reciprocating forces on both the bracket mount and the bracket.

In another aspect, some implementations include a device configured to perform any of the methods described herein (e.g., A1-A7 described above).

In yet another aspect, some implementations include a system including any of the devices described herein (e., B1-B8 described above) to perform any of the methods described herein (e.g., A1-A7 described above).

In yet another aspect, some implementations include a system with the means to perform any of the methods described herein (e.g., A1-A7 described above).

Thus, devices and systems are provided with methods for applying one or more orthodontic brackets, thereby increasing the accuracy, precision, effectiveness, efficiency, and user satisfaction with such devices and systems. Such methods may complement or replace conventional methods for applying one or more orthodontic brackets.

BRIEF DESCRIPTION OF THE DRAWINGS

For a better understanding of the various described implementations, reference should be made to the Description of Implementations below, in conjunction with the following drawings in which like reference numerals refer to corresponding parts throughout the figures.

FIGS. 9A-9C show perspective views of representative brackets in accordance with some implementations.

Like reference numerals refer to corresponding parts throughout the several views of the drawings.

DESCRIPTION OF IMPLEMENTATIONS

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, and devices have not been described in detail so as not to unnecessarily obscure aspects of the implementations.

Figure 1A:
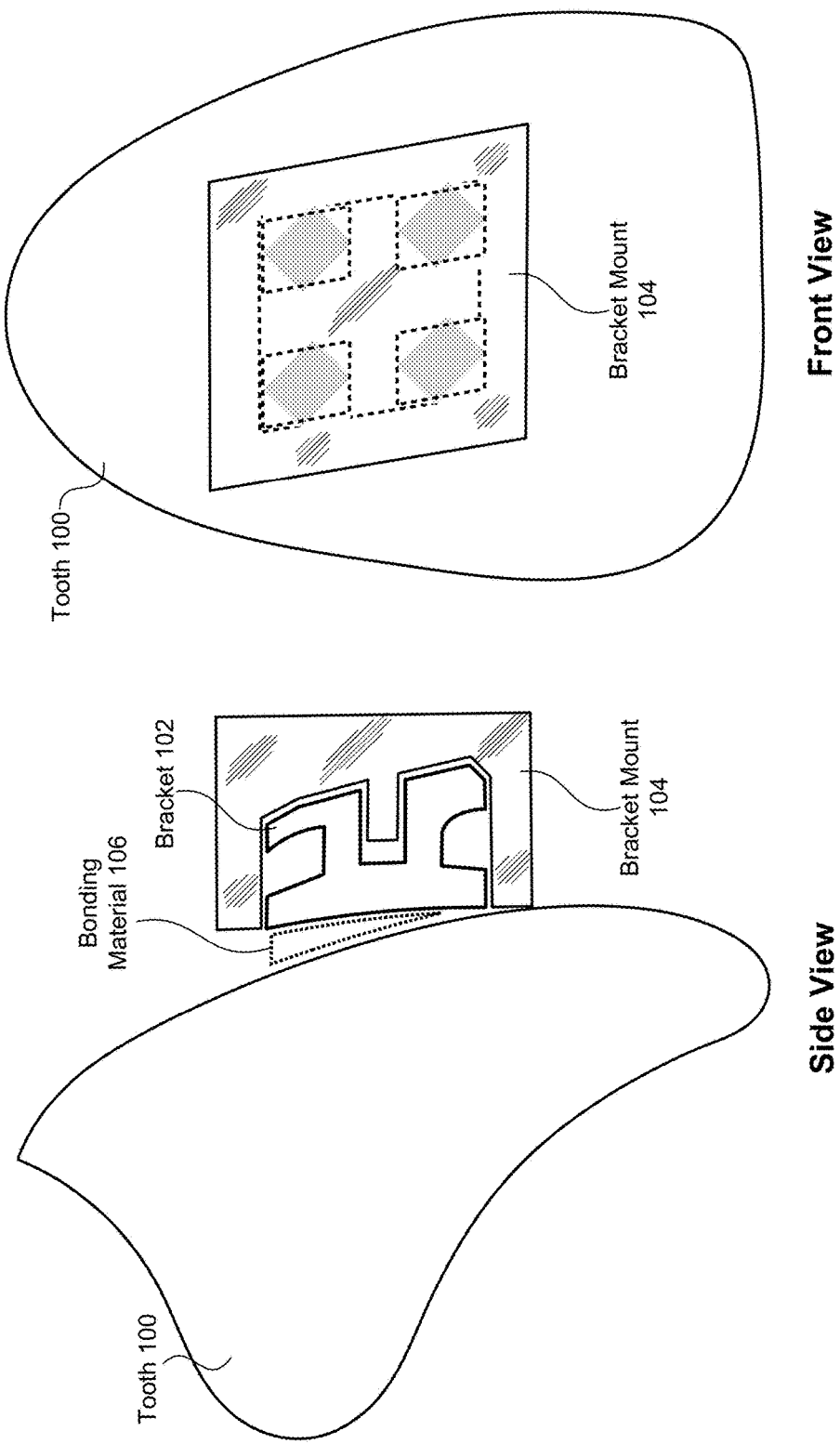
FIGS. 1A-1C show perspective views of representative bracket mounts in accordance with some implementations.
Figure 1B:
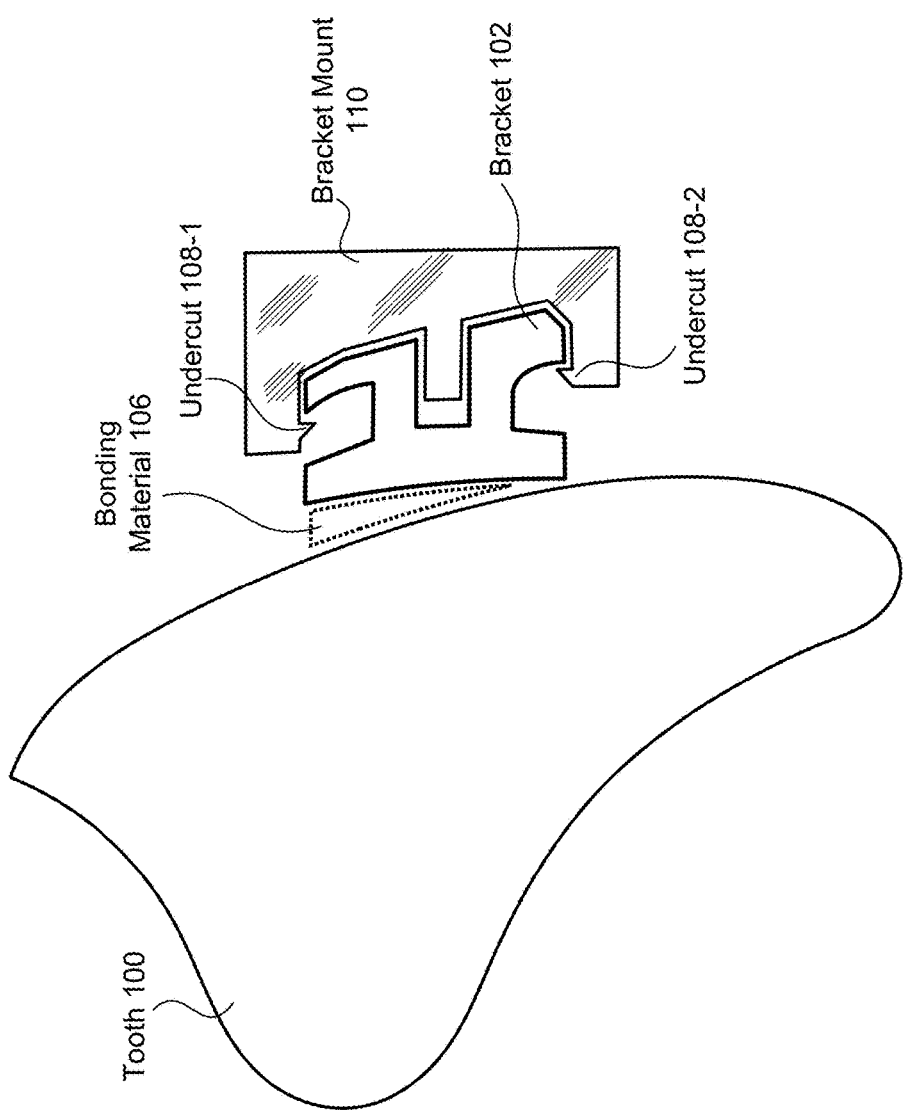
Figure 1C:
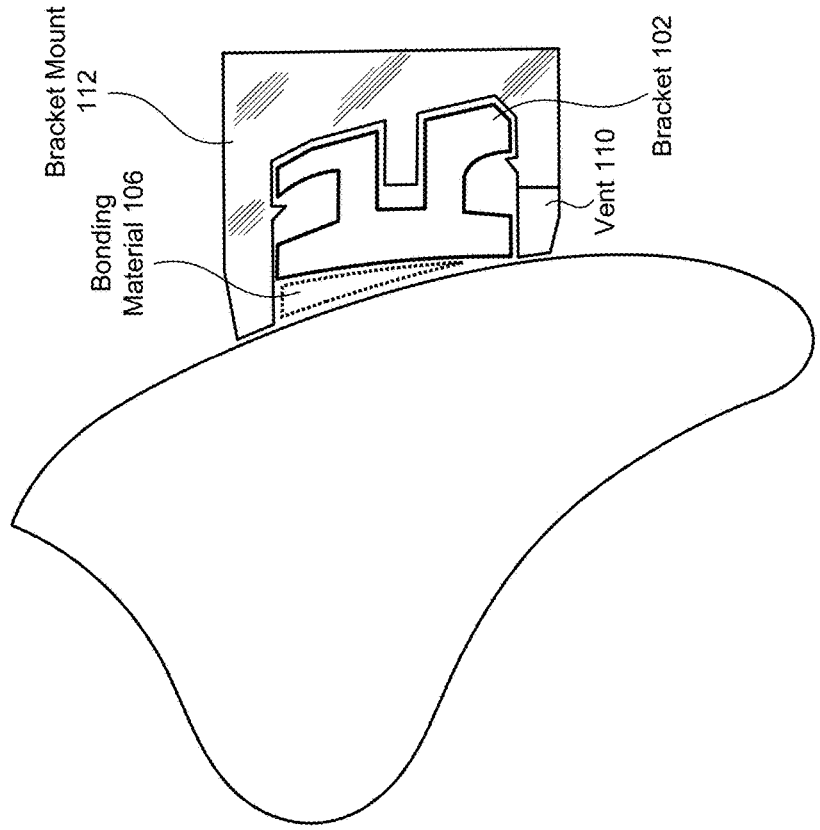
Figure 1C:
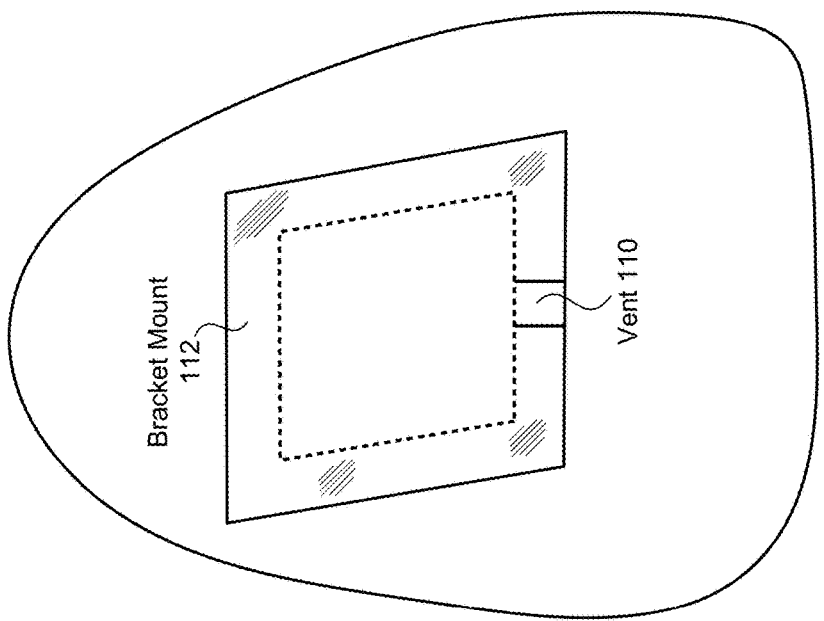

FIGS. 1A-1C show perspective views of bracket mounts in accordance with some implementations. FIG. 1A shows a side and front view of a bracket 102 affixed to a tooth 100. FIG. 1A also shows a bracket mount 104 configured to apply the bracket 102 to the tooth 100 and bonding material 106 to affix the bracket 102 to the tooth. The bracket mount 104 is configured to optimize positioning of the bracket 102 on the tooth 100. For example, the bracket mount 104 is configured to optimize an attachment angle between the tooth 100 and the bracket 102. In some implementations, the attachment angle is maintained by filling a gap between the bracket 102 and the tooth 100 with bonding material 106. In some implementations, the bracket mount 104 is produced based on a mapping of a patient's teeth (e.g., a 3-D mapping). In some implementations, optimizing positioning of the bracket 102 on the tooth includes optimizing a relationship between the bracket 102 and a bracket wire configured to couple the bracket 102 to other brackets on the patient's teeth. In some implementations, the relationship between the bracket 102 and the bracket wire is optimized such that force applied to the tooth through the bracket 102 and the bracket wire shifts the tooth in a desired direction. In some implementations, the relationship between the bracket 102 and the bracket wire is optimized such that a force applied to the bracket 102 from the bracket wire is more evenly distributed across the bracket 102. In some implementations, the bracket mount 104 is configured to suspend the bracket 102 in an optimal position with respect to the tooth 100 while bonding material is utilized to affix the bracket 102 to the tooth 100. In some implementations, the bracket mount's interior surface is configured such that it is a negative of the bracket surface for an anterior-posterior fit. In some implementations, the bracket mount 104 is configured to have a vertical slot, horizontal slot, or both for vertical and transverse fitting. In some implementations, the bracket mount 104 includes a pair of parallel surfaces vertical to the tooth surface and 90 degrees to the vertical or horizontal slot. In some implementations, the bracket mount 104 includes an undercut to facilitate separation of the bracket mount from the bracket 102 after the bracket has been mounted to the tooth 100.

FIG. 1B shows a side view of the bracket 102 affixed to the tooth 100 with bonding material 106. FIG. 1B further shows bracket mount 110 configured to selectively couple to the bracket 102 and apply the bracket 102 to the tooth 100. The bracket mount 110 differs from the bracket mount 104 in FIG. 1A in that it includes undercuts 108, undercut 108-1 on the top of the bracket mount 110 and undercut 108-2 on the bottom of the bracket mount 110. In some implementations, the bracket mount 110 includes a single undercut 108 (e.g., only undercut 108-1 or only undercut 108-2). In some instances, the undercuts 108 facilitate removal of excess bonding material 106 and, in some implementations and instances, decrease the likelihood of the bracket mount 110 becoming affixed to the tooth 100 via the bonding material 106. In some instances, the undercuts 108 facilitate separation of the bracket mount 110 from the bracket 102 after the bracket has been mounted to the tooth 100.

FIG. 1C shows a side view and a front view of the bracket 102 affixed to the tooth 100 with bonding material 106. FIG. 1C further shows bracket mount 112 configured to selectively couple to the bracket 102 and apply the bracket 102 to the tooth 100. The bracket mount 112 differs from the bracket mount 104 in FIG. 1A in that it includes a vent 110 to facilitate the removal of excess bonding material 106 and has a positive release angle at the top of the mount. The positive release angle at the top of the bracket mount 112 decreases the likelihood of the bracket mount 112 becoming affixed to the tooth 100 via the bonding material 106. In some implementations, the positive release angle minimizes binging of the bracket mount to the tooth by bonding material 106 (e.g., excessive bonding material). In some implementations, the bracket mount 112 includes the vent 110 but does not have a positive release angle. In some implementations, the bracket mount 112 has a positive release angle, but does not include the vent 110. In some implementations, the bracket mount 112 is configured to control the flow of bonding material 106 (e.g., excessive bonding material 106) during cementation of the bracket 102 to the tooth 100. In some implementations, the vent 110 is configured to control the flow of bonding material 106 (e.g., excessive bonding material 106) during cementation of the bracket 102 to the tooth 100. In some implementations, the vent 110 is configured to enable excess bonding material 106 to escape from the bonding area to prevent misalignment of the bracket 102, or weakening of the bond between the bracket 102 and the tooth, during and/or after the cementing process. In some implementations, the vent 110 is located on an occlusal side of the bracket mount. In some implementations, the vent 110 is located on a gingival side of the bracket mount. In some implementations, the vent 110 is located so as to be remote from a bulk of the bonding material 106.

Figure 1D:
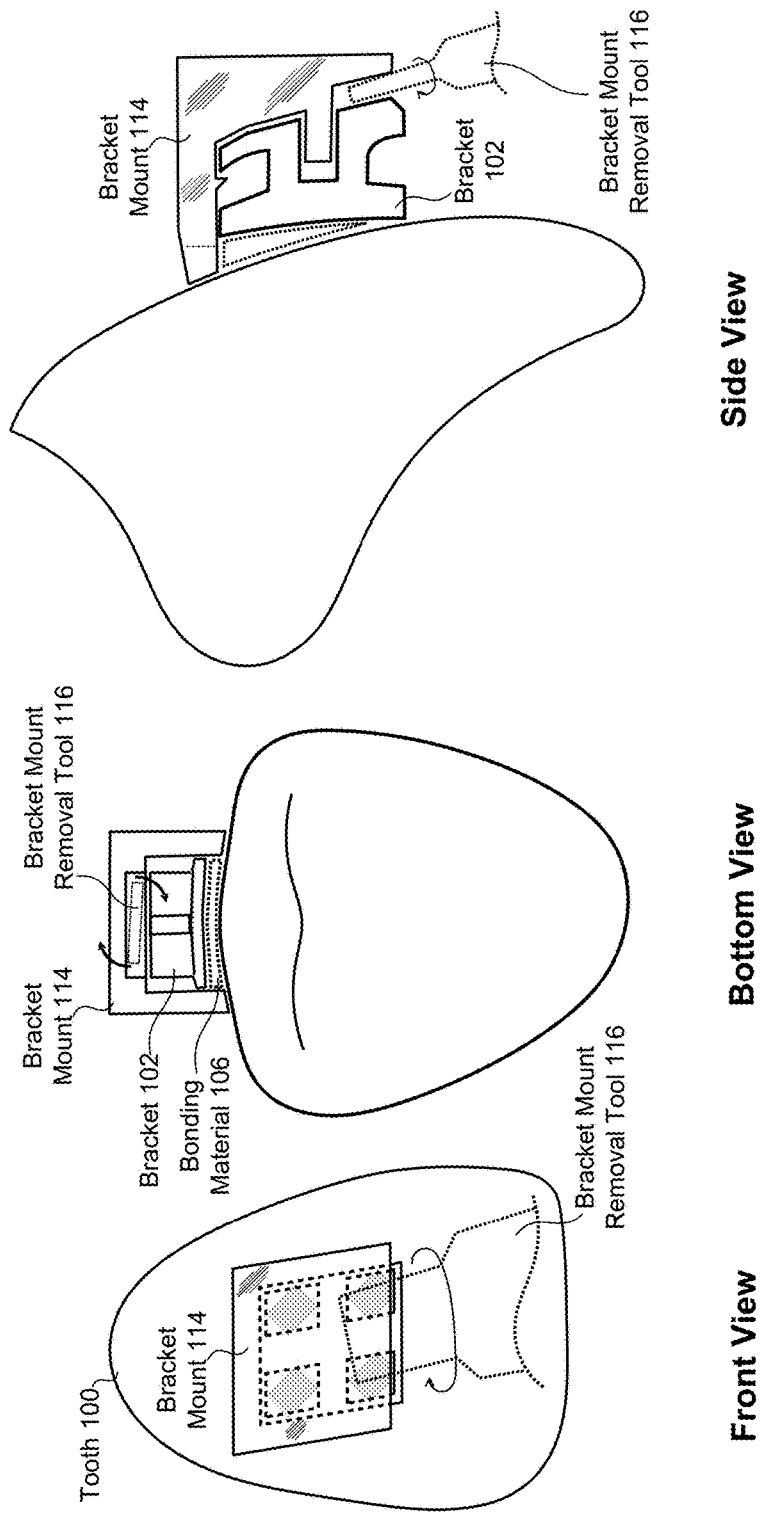
FIG. 1D shows perspective views of a representative bracket mount and representative bracket mount removal tool in accordance with some implementations.

FIG. 1D shows perspective views of a bracket mount and bracket mount removal tool in accordance with some implementations. FIG. 1D shows a front view, bottom view, and side view of a bracket 102 affixed to a tooth 100 with bonding material 106. FIG. 1D also shows a bracket mount 114 coupled to the bracket 102 and a bracket mount removal tool 116 (also sometimes called a bracket mount de-coupling tool). The bracket mount removal tool 116 is configured to de-couple the bracket mount 114 from the bracket 102 while minimizing the potential for the bracket 102 to become detached from the tooth 100. The bracket mount removal tool 116 is configured to slide between the bracket mount 114 and the bracket 102. A twisting motion applied to the bracket mount tool 116 results in a force that separates the bracket mount 114 from the bracket 102 without separating the bracket 102 from the tooth 100. In some implementations, the bracket mount 114 and/or the bracket mount tool 116 are configured so as to release the bracket mount from the bracket 102 with minimized risk of dislodging the bracket from the tooth (e.g., by minimizing a force pulling the bracket 102 away from the tooth 100). In some implementations, the bracket mount 114 and/or the bracket mount tool 116 are configured so as to release the bracket mount from the bracket 102 with minimized weakening of the bonding material 106 (e.g., by minimizing a force pulling the bracket 102 away from the bonding material 106). In some implementations, the bracket mount includes a release slit configured to allow access by the bracket mount tool to a space between the bracket mount and the bracket. In some implementations, the bracket mount tool is configured to apply a rotating force that concurrently pushes the bracket toward the tooth and the bracket mount away from the bracket.

Figure 2A:
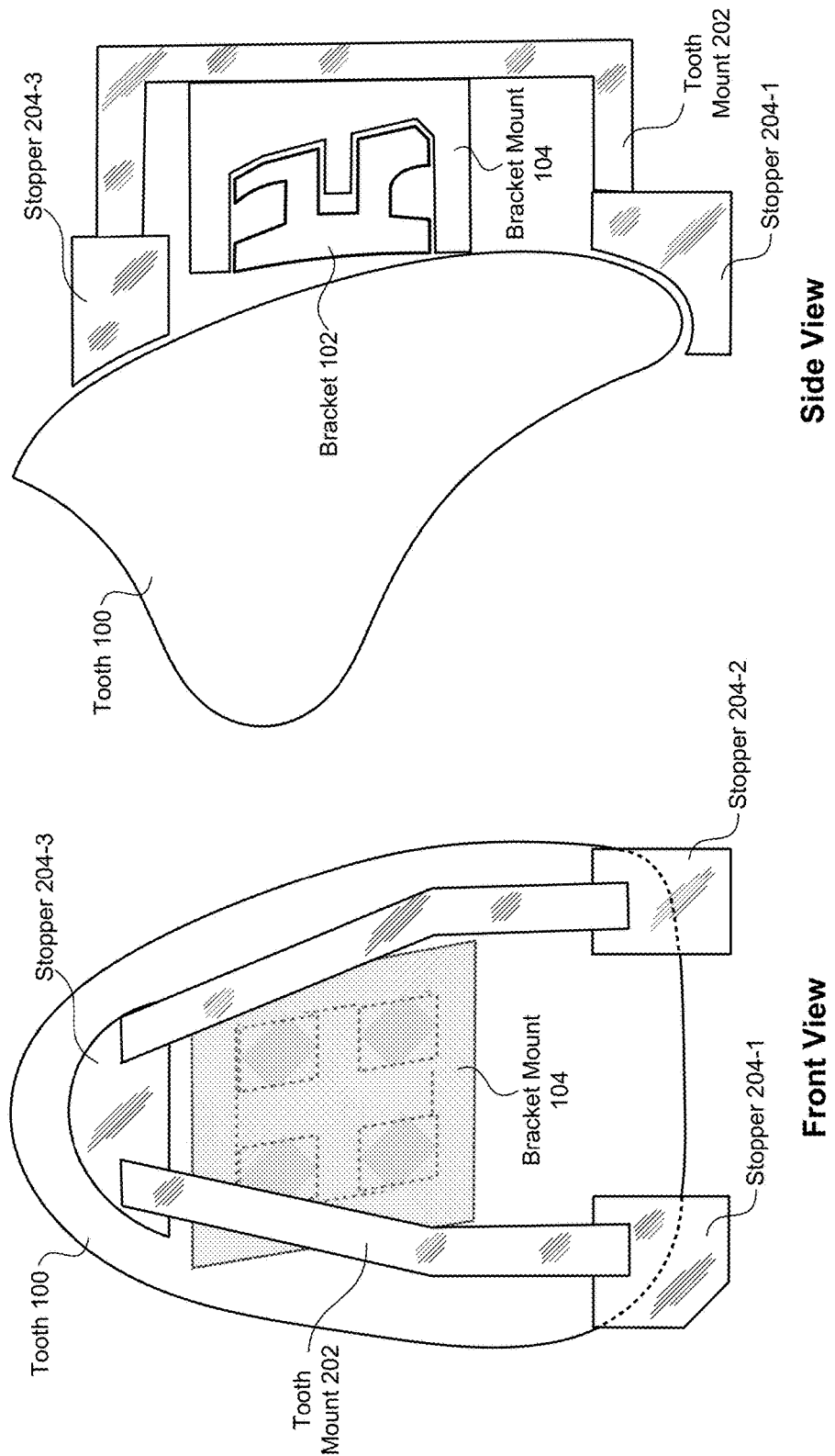
FIGS. 2A-2J show perspective views of representative tooth mounts in accordance with some implementations.

FIGS. 2A-2H show perspective views of tooth mounts in accordance with some implementations. FIG. 2A shows a front view and side view of a bracket 102 positioned on a tooth 100. FIG. 2A further shows the bracket 102 positioned via a bracket mount 104 and tooth mount 202. The tooth mount 202 is configured to align and stabilize the bracket 102 on the tooth 100. For example, the bracket mount 104 is configured to optimize an attachment angle between the tooth 100 and the bracket 102 and the tooth mount 202 is configured to attach the bracket 102 at an optimal location on the tooth 100. In some implementations, the bracket mount 104 and the tooth mount 202 comprise a single mount (e.g., are connected together such that they are indistinguishable from one another). In some implementations, the tooth mount 202 includes multiple stoppers 204 (e.g., stopper 204-1, 204-2, and 204-3 in FIG. 2A) for coupling to a tooth. For example, a stopper (e.g., stopper 204-1) is configured so as to precisely fit a particular location on the tooth 100. In some implementations, the bracket mount 104 is configured to position the bracket 102 at a particular orientation on the tooth 100. In some implementations, the tooth mount 202 is configured to position the bracket 102 at a particular location on the tooth 100. In some implementations, the tooth mount 202 includes a plurality of stoppers 204 connected via a plurality of connectors. In some implementations, the tooth mount 202 is produced based on a mapping of the patient's teeth (e.g., the tooth mount is 3-D printed). In some implementations, the bracket mount 104 and the tooth mount 202 are produced from a single piece of plastic (e.g., using a 3-D printer).

In some implementations, the tooth mount 202 is configured to use one or more tooth surfaces as reference points for positioning the bracket 102 on the tooth. In some implementations, the tooth mount includes one or more incisal stoppers (e.g., stoppers 204-1 and 204-2). In some implementations, the tooth mount includes a plurality of incisal stoppers to improve stability. In some implementations, the tooth mount includes a bracket or tooth identifier, such as a chiseled corner. For example, the stopper 204-1 in FIG. 2A includes a chiseled corner as a bracket identifier. In some implementations, the tooth mount 202 is configured to use the incisal edge of the tooth as a vertical stop. In some implementations, one or more of the stoppers (e.g., stopper 204-1) include an undercut to couple to the tooth (e.g., an undercut configured to couple to an incisal edge. In some implementations, the undercut is configured to be minimized so as to substantially match an insertion path to a removal path for the tooth mount 202. In some implementations, the tooth mount is configured such that the insertion path and the removal path are substantially vertical with respect to the face of the tooth. In some implementations, the tooth mount includes a incisal stopper and an occlusal stopper, distinct from the incisal stopper (e.g., to facilitate bracket and/or bracket base cleaning).

Figure 2B:
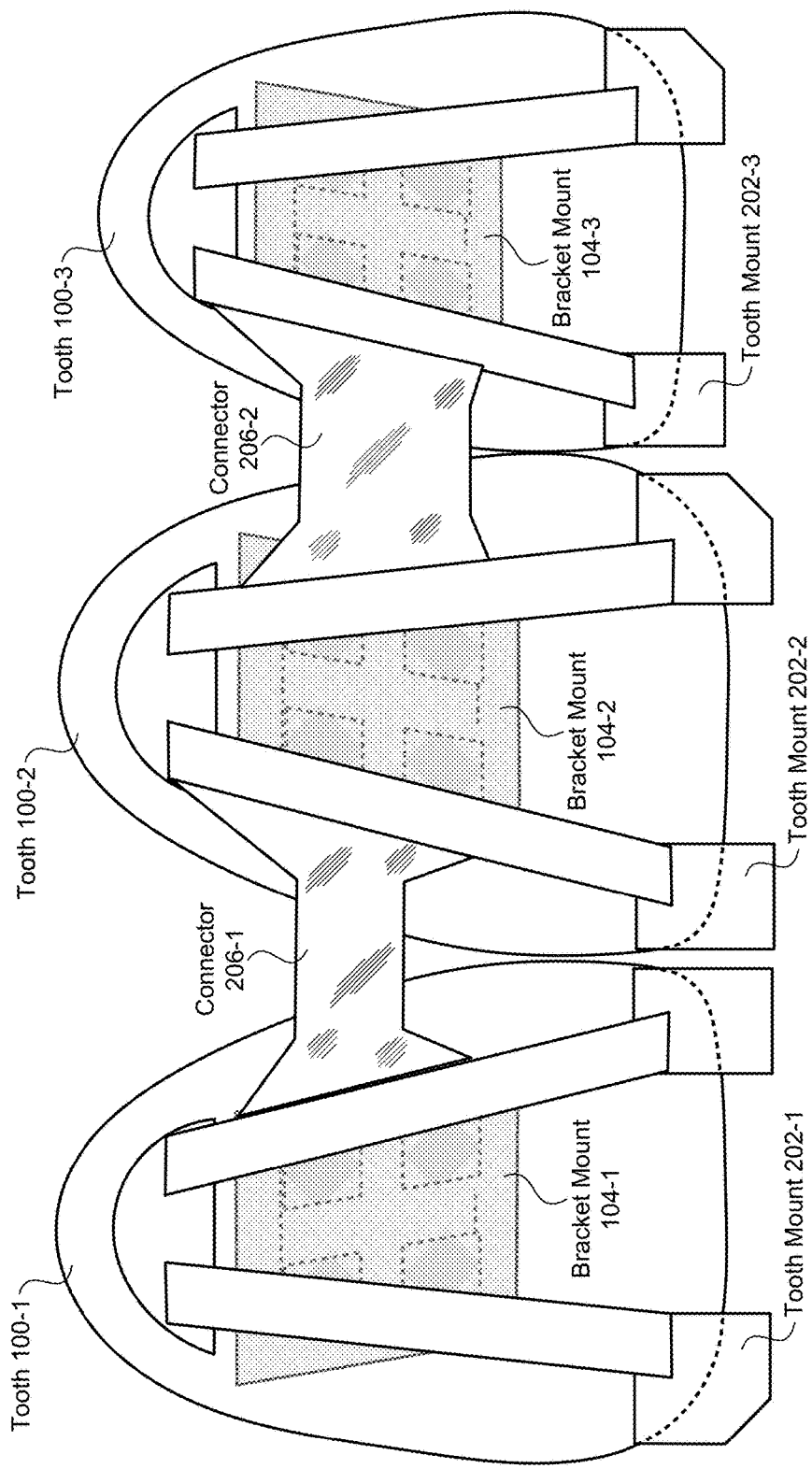

FIG. 2B shows a front view of a patient's teeth 100 with a bracket mount 104 and tooth mount 202 coupled to each tooth 100 (e.g., bracket mount 104-1 and tooth mount 202-1 coupled to tooth 100-1). FIG. 2B further connectors 206 connecting the tooth mounts 202 to one another. For example, connector 206-1 connects tooth mount 202-1 to tooth mount 202-2. In some implementations, the connectors 206 are configured based on relative positioning of the teeth 100. For example, the connector 206-1 is configured so as to optimize positioning of tooth mount 202-1 on tooth 100-1 and positioning of tooth mount 202-2 on tooth 100-2. In some implementations, a connector 206 has a width based on an amount of force to be applied to the adjacent teeth (e.g., the larger the amount of force the wider the connector 206). For example, FIG. 2B shows connector 206-2 having a wider profile than connector 206-1. In some implementations, the connectors are configured to couple multiple tooth mounts for arch or sectional cementation. In some implementations, the connectors are configured to provide rigidity to hold the tooth mounts together in precise positioning. In some implementations, the connectors 206 have varying thickness to provide flexibility for engaging a posterior undercut.

Figure 2C:
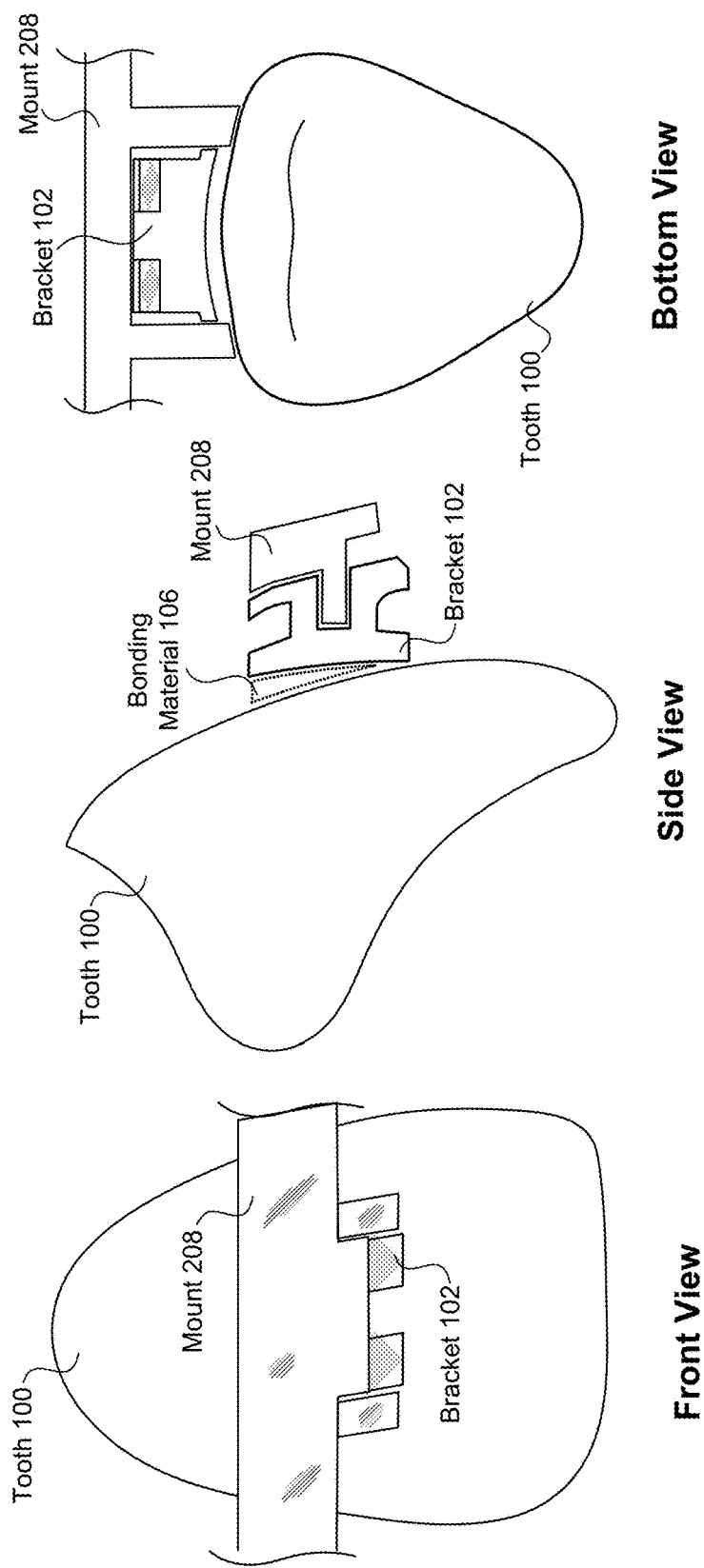

FIG. 2C shows a front view, bottom view, and side view of a bracket 102 affixed to a tooth 100 with bonding material 106. FIG. 2C further shows a mount 208 configured to position the bracket 102 at an optimal position and/or an optimal angle on the tooth 100. In some implementations, the mount 208 comprises a bracket mount.

Figure 2D:
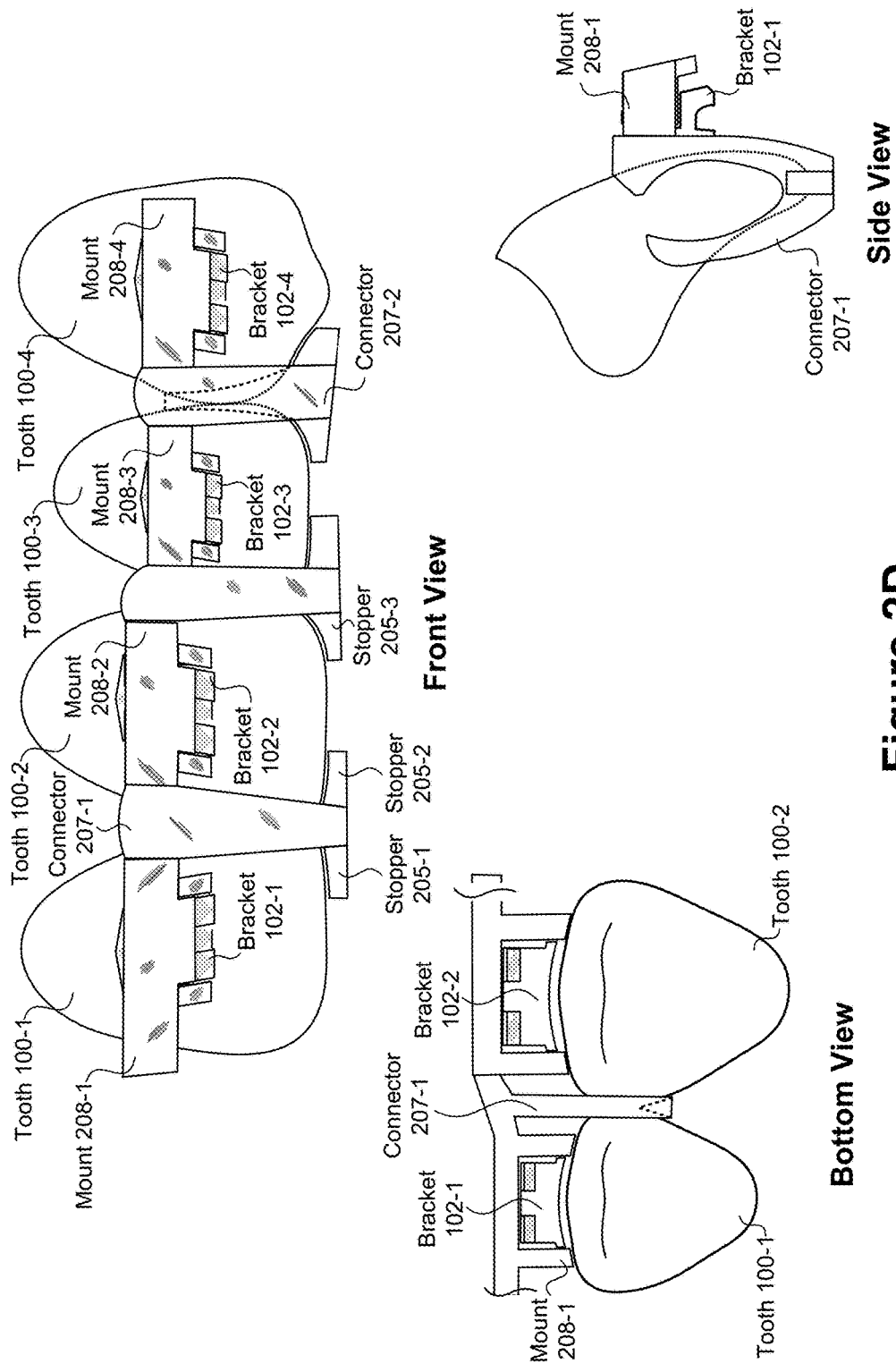

FIG. 2D shows a front view, bottom view, and side view of brackets 102 positioned on teeth 100. FIG. 2D further shows mounts 208 configured to position the brackets 102 at optimal positions and/or angles on the teeth 100. For example, the mount 208-1 positions the bracket 102-1 on the tooth 100-1 and the mount 208-2 positions the bracket 102-2 on the tooth 100-2. FIG. 2D also shows connectors 207 connecting the mounts 208 to one another. For example, connector 207-1 connects mount 208-1 to mount 208-2. In accordance with some implementations, the connectors 207 are configured to position the brackets 102 at optimal positions on the teeth 100. The connectors 207 optionally include stoppers 205 for aligning the brackets 102 with the teeth 100. For example, connector 207-1 includes stoppers 205-1 and 205-2. The stopper 205-1 is configured to align and stabilize mount 208-1 on tooth 100-1 and the stopper 205-2 is configured to align and stabilize mount 208-2 on tooth 100-2 (in conjunction with stopper 205-3). As shown in the side view of FIG. 2D, in some implementations, the connectors 207 are configured to couple to a front portion, back portion, and bottom portion of the tooth. In some implementations, the connectors 207 are configured to couple to a front portion and a bottom portion of the tooth, but not a back portion. In some implementations, the stoppers 205 are configured to provide a visual fit-check for the mounts 208. In some implementations, as illustrated in the side view, the connectors 207 are configured to couple to a buccal undercut and a lingual undercut of the patient (e.g., to provide stability and positioning of the mounts 208).

Figure 2E:
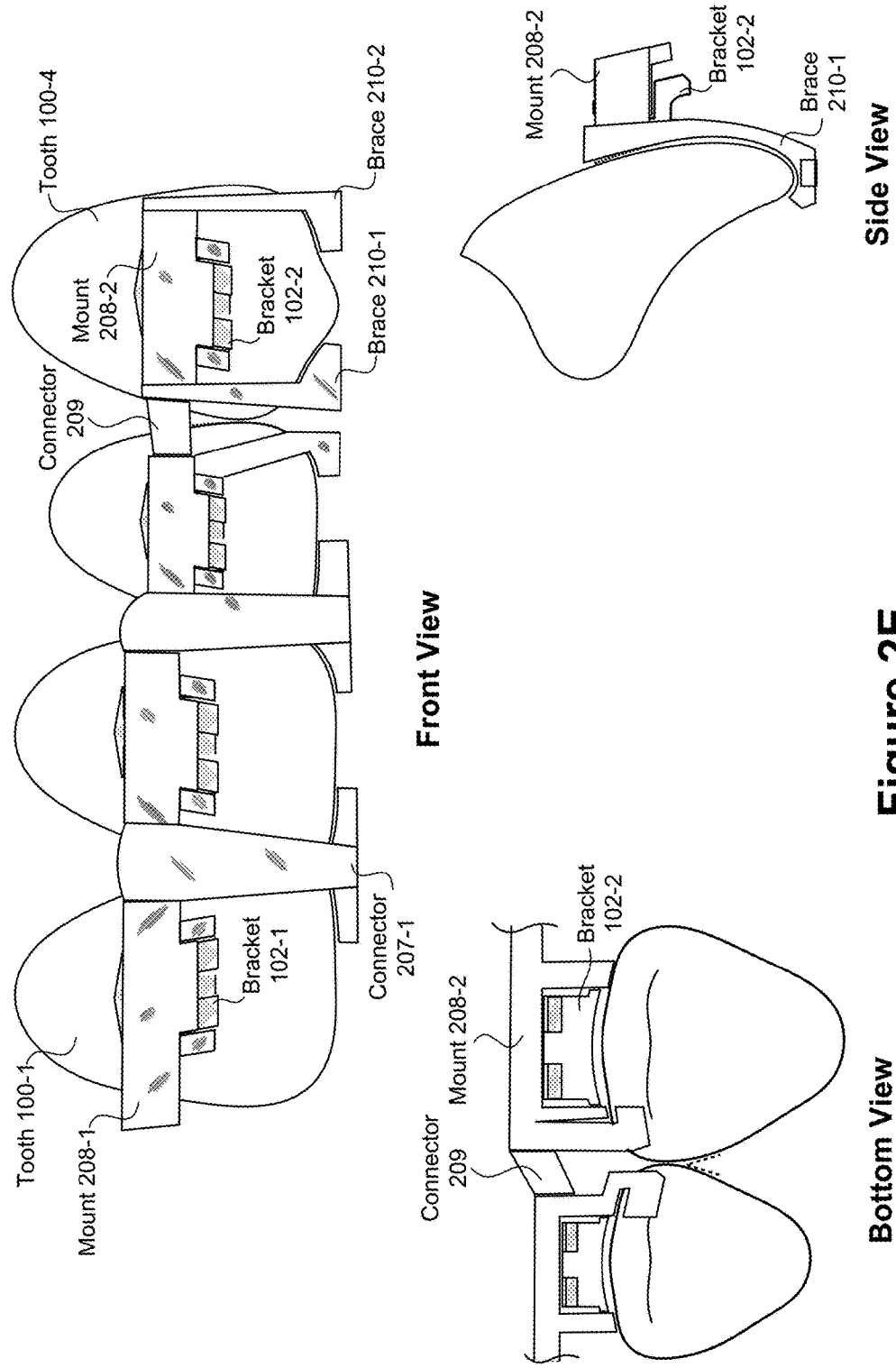

FIG. 2E shows a front view, bottom view, and side view of brackets 102 positioned on teeth 100. FIG. 2E further shows mounts 208 configured to position the brackets 102 at optimal positions and/or angles on the teeth 100. In FIG. 2E mount 208-2 is coupled to braces 210 and connector 209. In some implementations, braces 210 compose a tooth mount. As shown in the side view of FIG. 2E, in some implementations, the braces 210 are configured to couple to a front portion and bottom portion of the tooth. In some implementations, the braces 210 are configured to couple to a front portion, back portion, and bottom portion of the tooth.

Figure 2F:
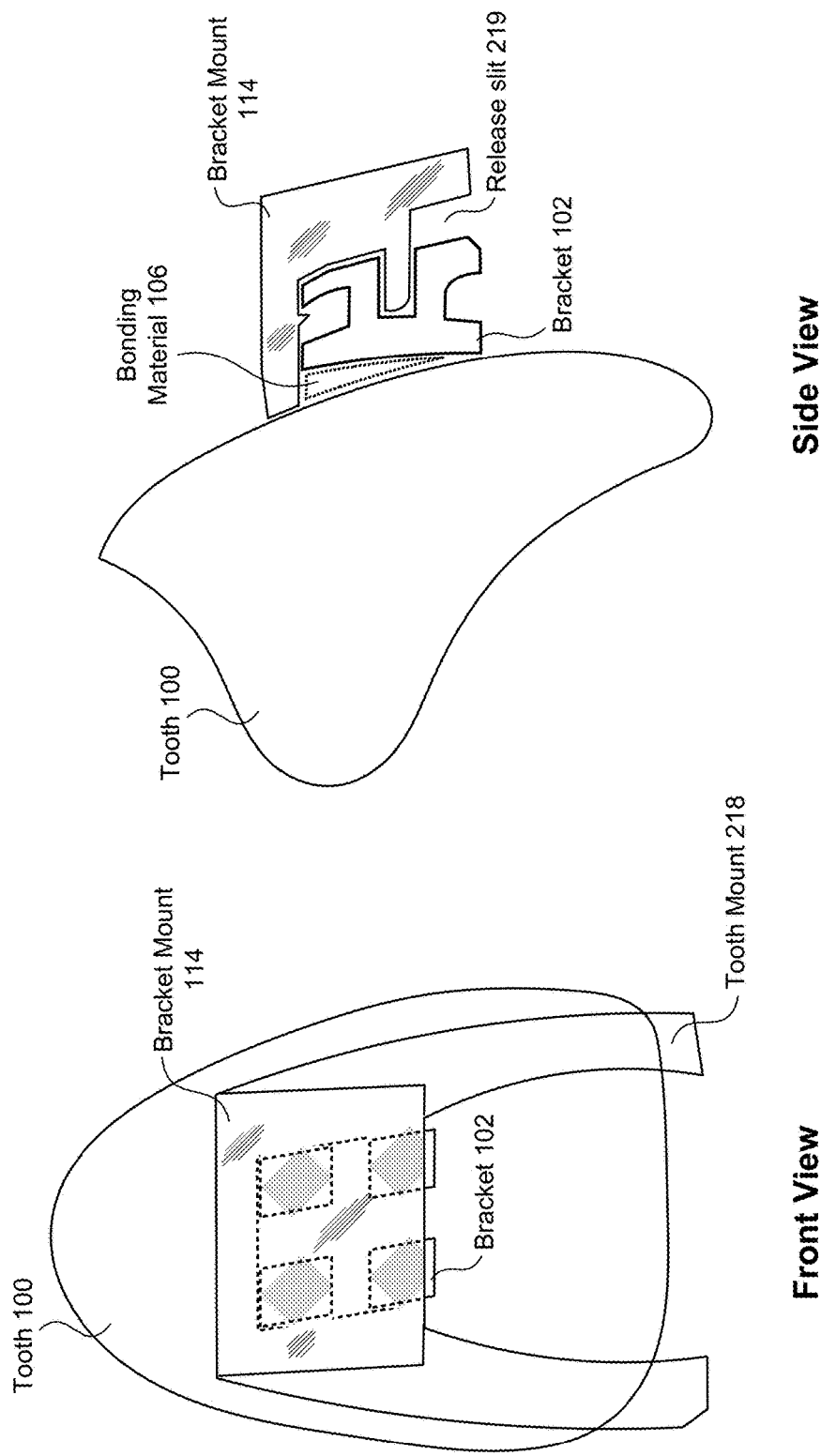

FIG. 2F shows a front view and side view of a bracket 102 affixed to a tooth 100 via bonding material 106. FIG. 2F also shows a bracket mount 114 and tooth mount 218. FIG. 2F also shows a release slit 219 between the bracket mount 114 and the bracket 102. In some implementations, the release slit 219 is configured so as to facilitate separation of the bracket mount from the bracket after the bracket is bonded or affixed to the tooth. In some implementations, the tooth mount 218 includes two stoppers configured to couple to the bottom of the tooth. In some implementations, the tooth mount 218 and the bracket mount 114 comprise a single mount. In some implementations, the tooth mount 218 is configured so as to facilitate cleaning of the bottom of the bracket and/or the surface of the tooth beneath the bracket (e.g., cleaning of excess bonding material). For example, tooth mount 218 is configured such that the bottom of the bracket and the surface of the tooth beneath the bracket are accessible for cleaning. In some implementations, as shown in FIG. 2F, the bracket mount 114 includes a positive release angle with respect to the tooth and an undercut. In some implementations, the bracket mount 114 is configured to have a custom and precise fit with the surface of the tooth (e.g., to optimize positioning of the bracket 102).

Figure 2G:
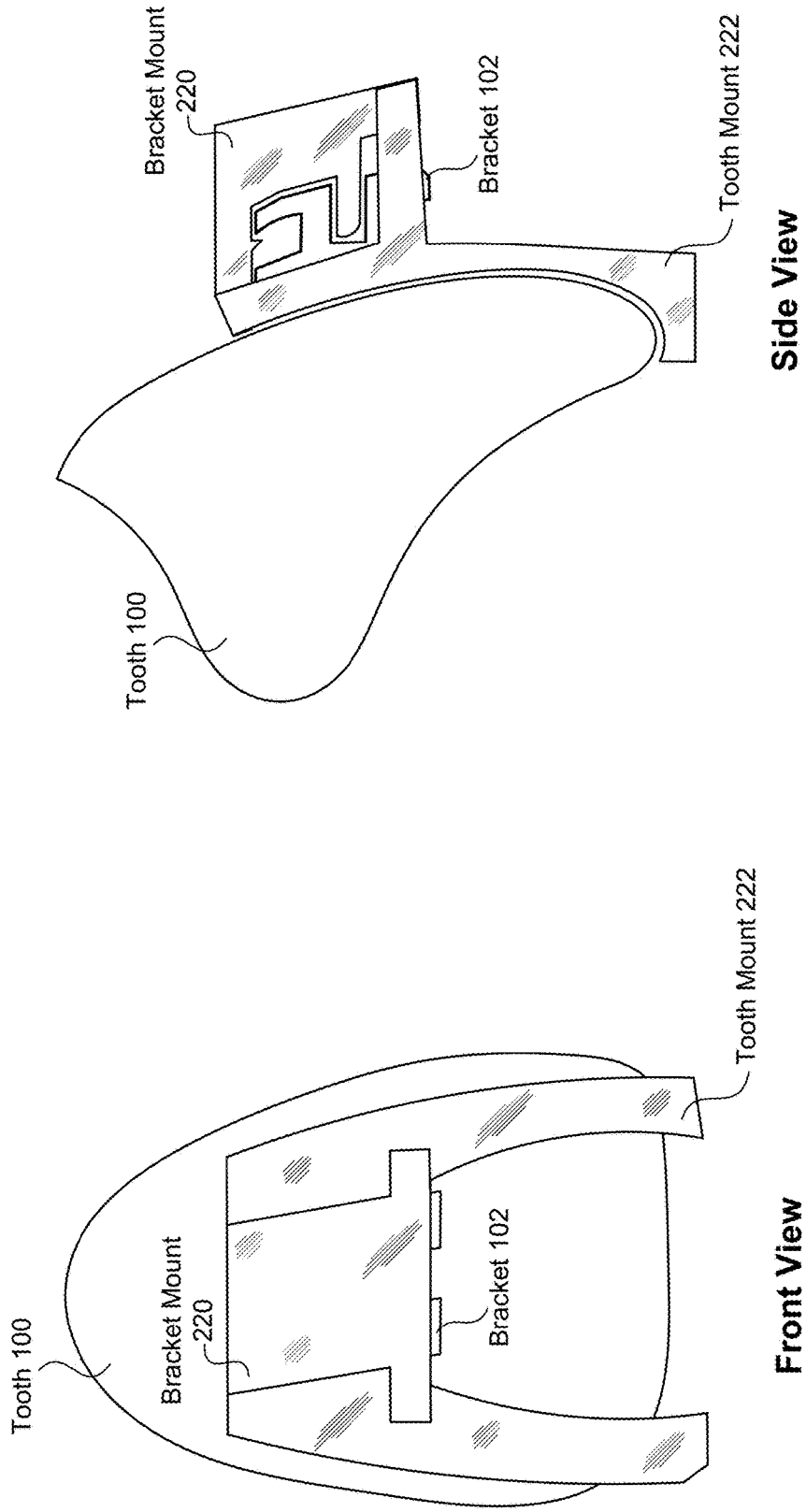

FIG. 2G shows a front view and side view of a bracket 102 positioned on a tooth 100. FIG. 2G also shows a bracket mount 220 and tooth mount 222. In some implementations, the tooth mount 222 includes two stoppers configured to couple to the bottom of the tooth. In some implementations, the tooth mount 222 and the bracket mount 220 comprise a single mount. As shown in FIG. 2G, the tooth mount 222 is configured to connect to the sides of the bracket mount 220 without completely enclosing the sides of the bracket 102. In some implementations, as shown in FIG. 2G, the tooth mount 220 is configured so as to provide a view (e.g., an open window) of the bracket (e.g., to facilitate checking of the bracket positioning). In some implementations, the tooth mount 220 is configured to have a custom and precise fit with the surface of the tooth (e.g., to optimize location and/or angle of the bracket with respect to the tooth).

Figure 2H:
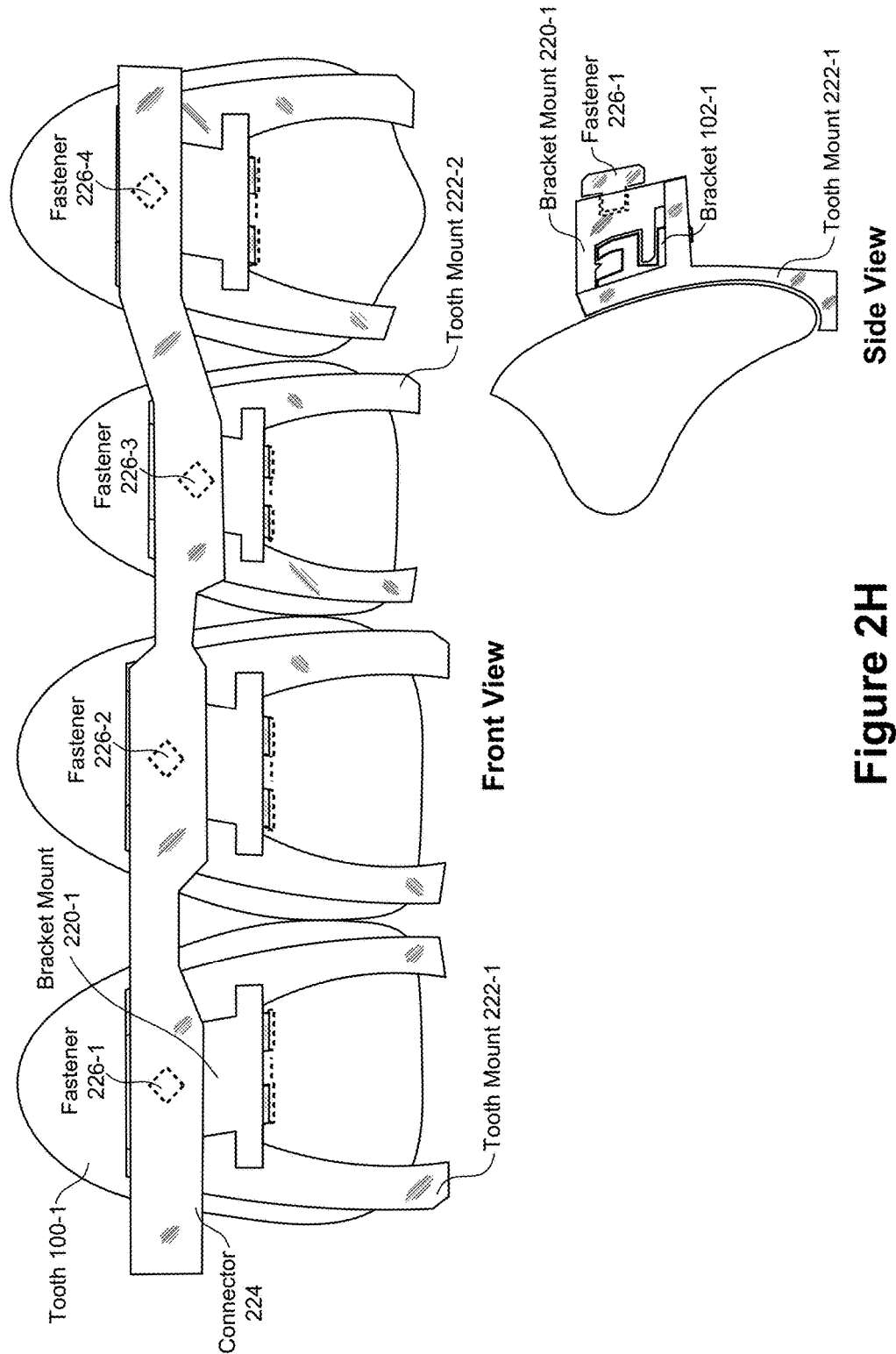

FIG. 2H shows a front view and side view of brackets 102 positioned on teeth 100. In FIG. 2H the tooth mounts 222 are coupled to one another via a connector 224. The tooth mounts 222 are coupled to the connector 224 via respective fasteners 226. For example tooth mount 222-1 is coupled to the connector 224 via fastener 226-1. In various implementations, the fasteners 226 comprise screws, bolts, clips, pins, or the like. In some implementations, each fastener 226 comprises a same type of fastener, while in other implementations, fasteners 226 include at least two distinct types of fasteners. In some implementations, the fasteners 226 connect the connector 224 to the bracket mounts 220. In some implementations, the fasteners 226 connect the connector 224 to the tooth mounts 222. In some implementations, as shown in FIG. 2H, the connector 224 is removably coupled to the tooth mounts 222. in some implementations, the connector 224 is removable coupled to at least one tooth mount 222 and fixedly coupled to at least other tooth mount 222. In some implementations, as shown in FIG. 2H, the connector 224 has a varying width (e.g., to optimize stability, positioning of brackets, and/or force distribution).

Figure 2I:
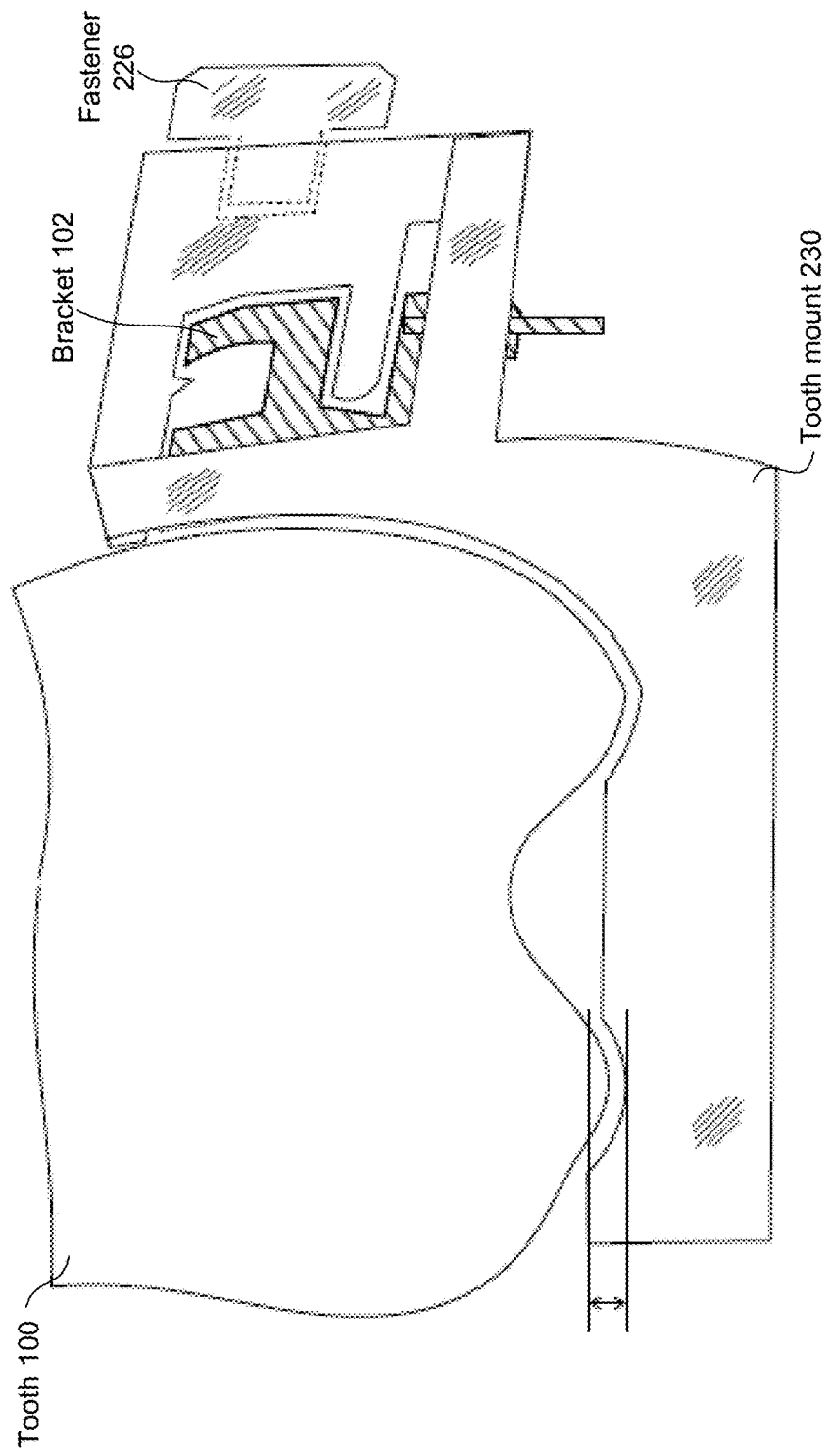

FIG. 2I shows a side view of a bracket 102 positioned on tooth 100. FIG. 2I also shows a representative tooth mount 230 configured to contact the occlusal tips and/or marginal ridge of the tooth 100. In accordance with some implementations, FIG. 2I also shows a fastener 226 for coupling the tooth mount 230 to a connector and one or more additional tooth mounts.

Figure 2J:
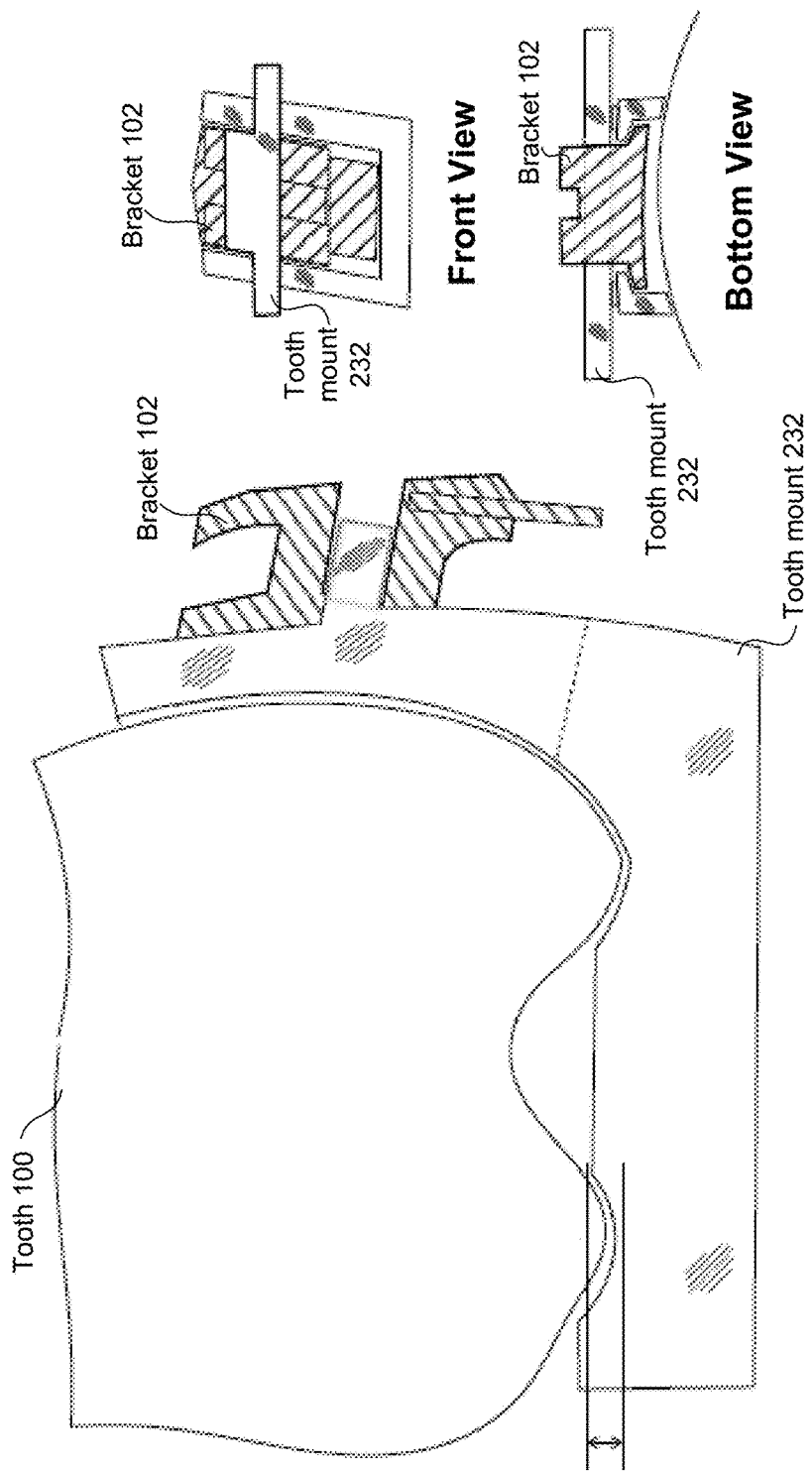

FIG. 2J shows a side view, front view, and bottom view of a bracket 102 positioned on tooth 100. FIG. 2J also shows a representative tooth mount 232 configured to contact the occlusal tips and/or marginal ridge of the tooth 100 (e.g., to provide stability and minimize wobbling).

Figure 3A:
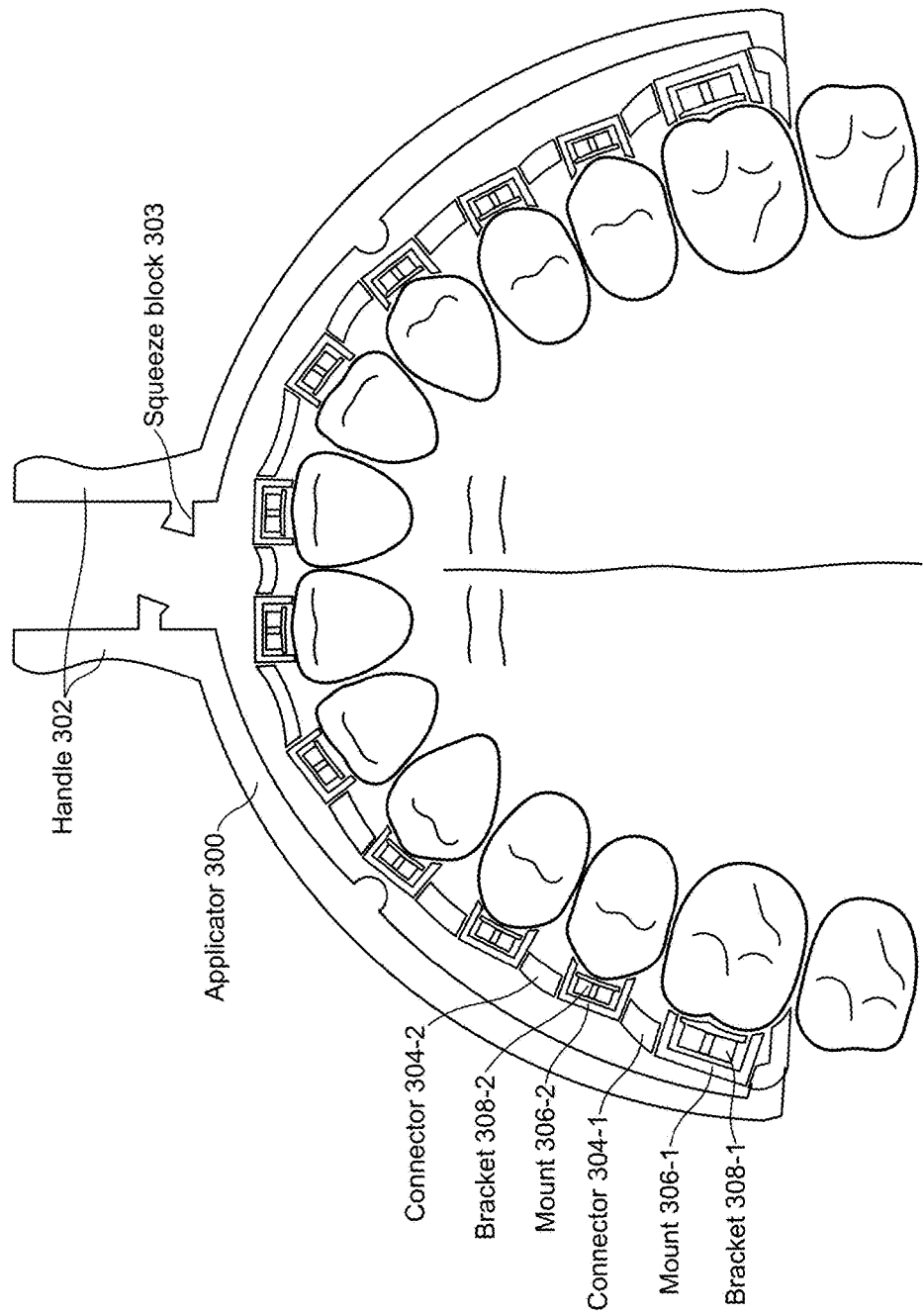
FIGS. 3A-3B show perspective views of representative bracket applicators in accordance with some implementations.
Figure 3B:
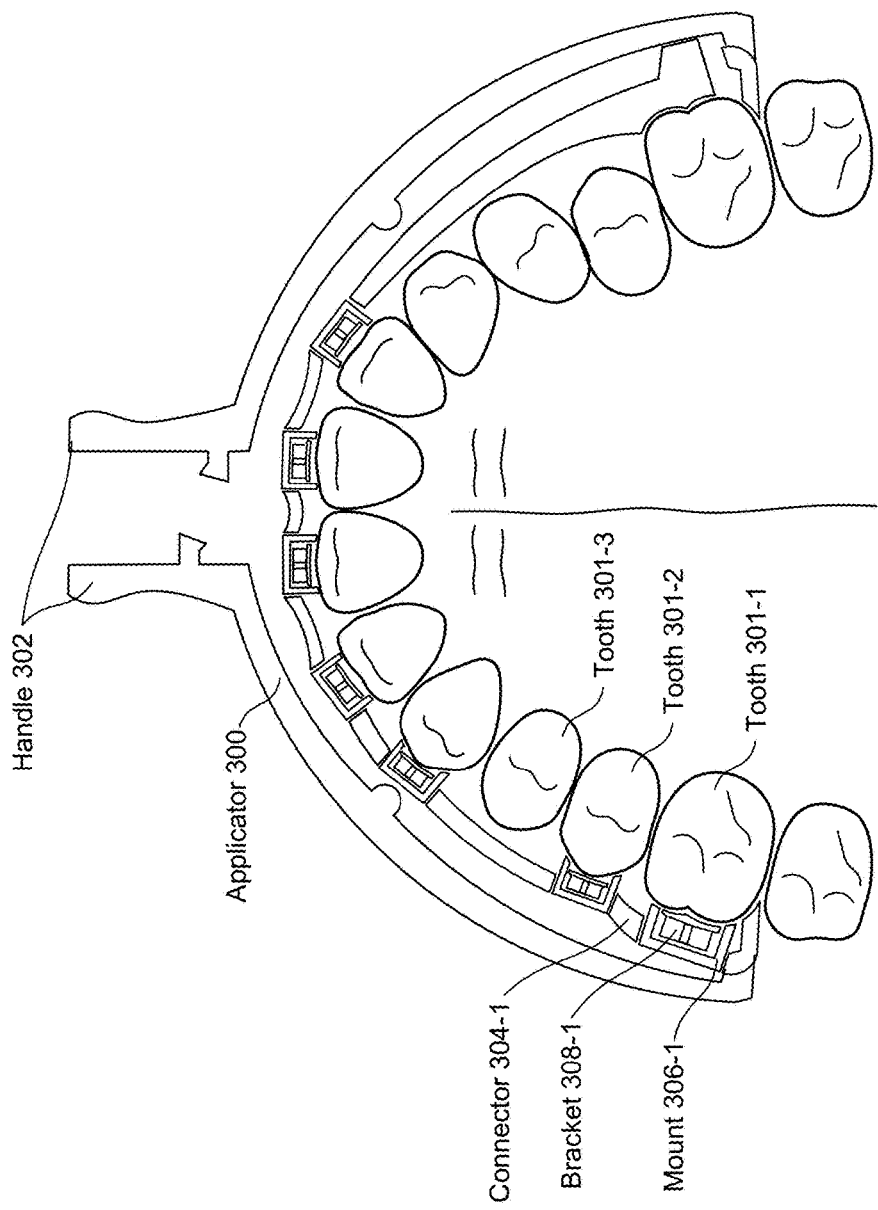

FIGS. 3A-3B show perspective views of bracket applicators in accordance with some implementations. FIG. 3A shows brackets 308 positioned on a set of teeth. FIG. 3A further shows mounts 306 (e.g., mounts 208, FIG. 2C) coupled to the brackets 308 (e.g., bracket 102, FIG. 1A) and connectors 304 (e.g., connectors 207, FIG. 2D) coupling the mounts 306 to one another. FIG. 3A also shows an applicator 300 for applying the brackets 308 to the patient's teeth. As shown in FIG. 3A the applicator 300 includes a handle 302. The handle 302 is configured such that squeezing the handle results in less force applied to the teeth through the applicator 300 and releasing the handle results in more force applied to the teeth through the applicator 300. In some implementations, the applicator 300 is removably coupled to the mounts 306 and connectors 304. In some implementations, the applicator 300 is fixedly coupled to the mounts 306 and connectors 304. In some implementations, the applicator 300 is configured to concurrently apply multiple brackets 308 to respective teeth for arch or sectional cementation. In some implementations, the applicator 300 is configured to provide rigidity to hold all of the mounts 306 in precise positioning.

In some implementations, the applicator 300 is configured to provide self-positioning and/or self-holding of bracket placement (e.g., during cementation of the brackets to the teeth). In some implementations, the applicator 300 has varying thickness along its length (e.g., to provide flexibility for engaging a posterior undercut). In some implementations, the applicator 300 includes a relatively thin anterior connector (e.g., for increased flexibility). In some implementations, the applicator 300 includes a relatively thick and/or rigid posterior connector (e.g., to prevent warping along the length of the applicator). In some implementations, the applicator 300 includes the handle 302 to facilitate placement of the applicator 300 in the patient's mouth and alignment of the brackets. In some implementations, the handle 302 comprises a squeezing handle for opening of the posterior displacement (e.g., to engage and disengage a posterior undercut). In some implementations, the handle 302 includes squeeze-blocks 303 configured to limit a squeeze distance (e.g., to prevent breaking of connectors 304). In some implementations, the squeeze-blocks 303 are configured to limit the squeeze distance so as to be sufficient to engage/disengage a posterior undercut without risk of breakage of connectors 304. In some implementations, the handle 302 includes a self-locking feature (e.g., using squeeze-blocks 303) to lock the handle in a squeezed position to facilitate placement of the applicator in a patient's mouth.

In some implementations, the applicator 300 is configured to facilitate positioning of orthodontic brackets on a patient's teeth. For example, the applicator 300 is configured to fit to particular locations on particular teeth to ensure proper placement. In some implementations, the applicator 300 is configured to facilitate positioning and mounting of a single orthodontic bracket. For example, a previously-set bracket has become dislodged and the applicator 300 is configured to replace only the dislodged bracket. In some implementations, the applicator 300 is produced based on a mapping of the patient's teeth (e.g., the applicator is 3-D printed).

Similar to FIG. 3A, FIG. 3B shows brackets 308 positioned on a set of teeth 301. FIG. 3B further shows mounts 306 coupled to the brackets 308 and connectors 304 coupling the mounts 306 to one another. FIG. 3B also shows an applicator 300 for applying the brackets 308 to the patient's teeth. As shown in FIG. 3B, in some implementations, the applicator 300 does not include a bracket 308, or bracket mount 306, for each tooth in the patient's set of teeth. For example, the applicator 300 includes a mount 306-1 and bracket 308-1 for tooth 301-1, but does not include a mount or bracket for tooth 301-3. In accordance with some implementations, the applicator 300 is configured so as to apply a bracket 308 on only a subset of the patient's teeth based on a type of orthodontic treatment required for, or selected, for the patient. In some instances, misalignment of the patient's teeth and/or a patient's treatment plan necessitates application of brackets to only a subset of the patient's teeth. In accordance with some implementations, the applicator 300 is configured to apply brackets to only a subset of the patient's teeth.

Figure 3C:
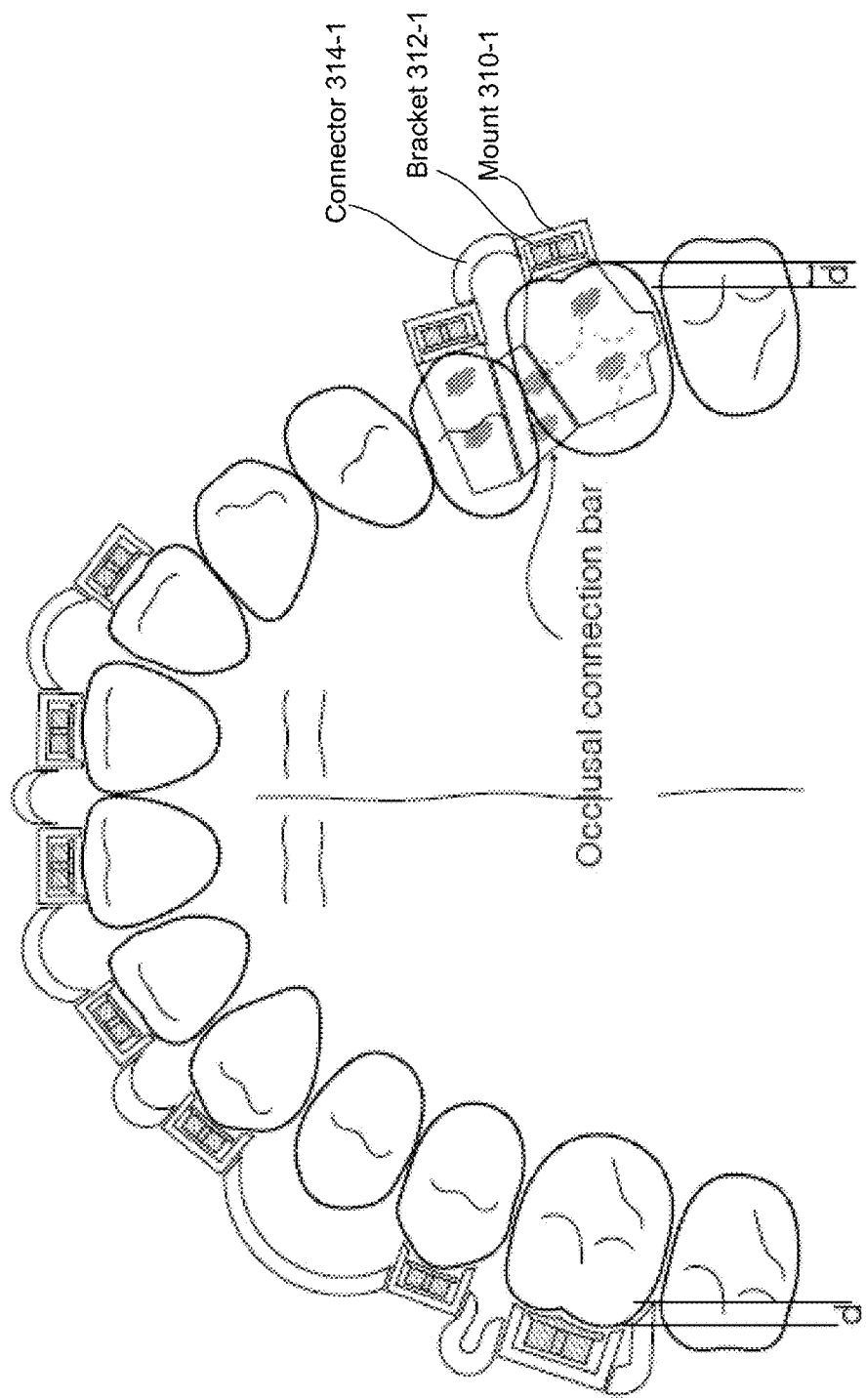
FIG. 3C shows a perspective view of representative tooth mounts with an occlusal bar in accordance with some implementations.

FIG. 3C shows brackets 312 positioned on a set of teeth. FIG. 3C further shows mounts 310 coupled to the brackets 312 and connectors 314 coupling the mounts 310 to one another. FIG. 3C also shows an occlusal connection bar configured to increase stability of the mounts 310 and facilitate precise positioning of the brackets 312 on the teeth. In some implementations, the occlusal connection bar is configured to act as a finger stop (e.g., enabling a finger to apply pressure and stability) during cementation of the brackets to the teeth. In some implementations, a shape and/or thickness of the occlusal connection bar is based on the positioning of the patient's teeth and/or requirement(s) of the orthodontic treatment for the patient. FIG. 3C further shows a distance, denoted as 'd', illustrating a displacement for engaging a posterior undercut.

Figure 4:
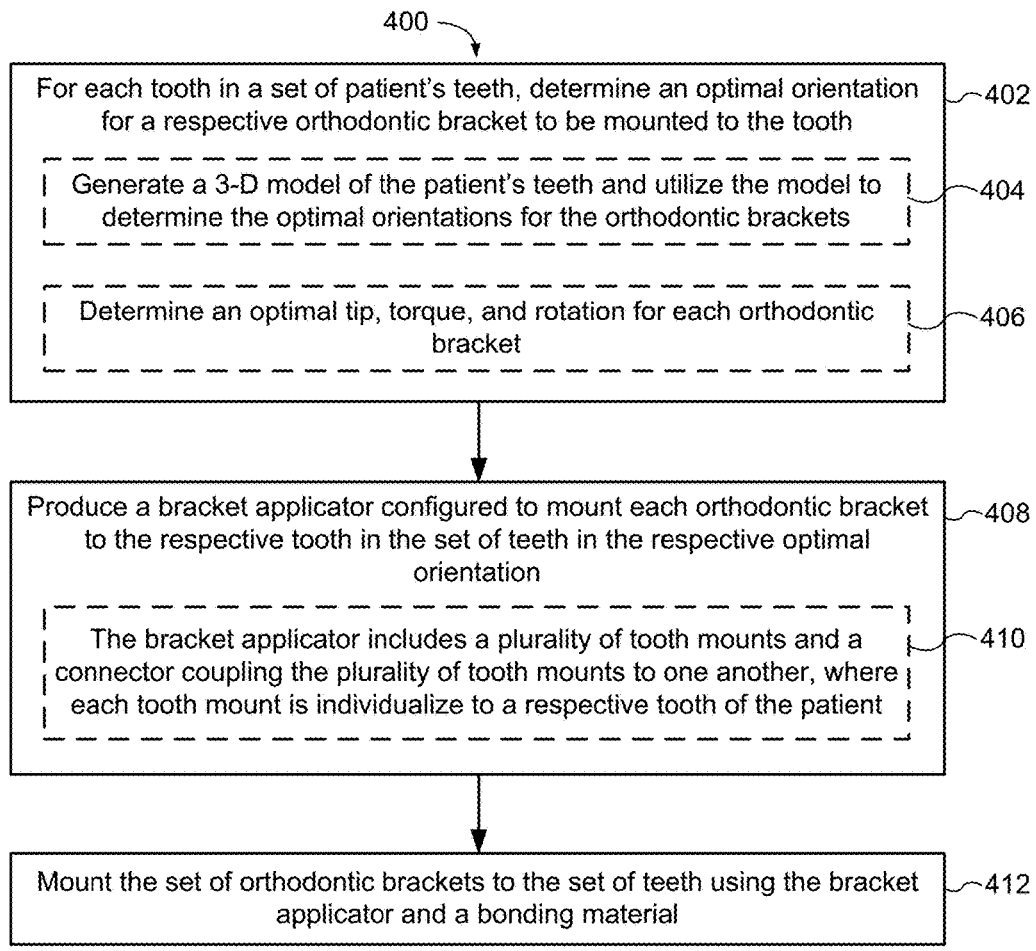
FIG. 4 is a flowchart illustrating a representative method for affixing orthodontic brackets to a patient's teeth in accordance with some implementations.

FIG. 4 is a flowchart illustrating a representative method 400 for affixing orthodontic brackets to a patient's teeth in accordance with some implementations.

For each tooth in a set of patient's teeth, determine (402) an optimal orientation for a respective orthodontic bracket to be mounted to the tooth. In some implementations, a 3-D model of the patient's teeth is generated (404). In some implementations, the optimal orientation is determined based on a 3-D model or mapping of the patient's teeth. In some implementations, an optimal tip, torque, and/or rotation for each orthodontic bracket is determined (406). In some implementations, determining the optimal orientation includes determining the optimal tip, torque, and/or rotation for each bracket.

A bracket applicator is produced (408). For example, applicator 300 shown in FIG. 3A. The bracket applicator is configured to mount each orthodontic bracket (e.g., bracket 102, FIG. 1A) to the respective tooth in the set of teeth in the respective optimal orientation. In some implementations, the bracket applicator includes (410) a plurality of tooth mounts (e.g., tooth mounts 202, FIG. 2B) and a connector (e.g., connectors 206, FIG. 2B) coupling the plurality of tooth mounts to one another, where each tooth mount is individualize to a respective tooth of the patient. In some implementations, the bracket applicator is made of plastic, polymer, or similar material. In some implementations, the bracket applicator is produced via a 3-D printing. In some implementations, producing the bracket applicator includes generating a computer model of the bracket applicator based on a patient's prescription. In some implementations, producing the bracket applicator includes generating a computer model of the bracket applicator based measurements of a patient's teeth (e.g., based on a mold of the patient's teeth). In some implementations, producing the bracket applicator includes printing, via a 3-D printer, the computer model of the bracket applicator.

The set of orthodontic brackets are mounted (412) to the set of teeth using the bracket applicator (e.g., applicator 300, FIG. 3A) and a bonding material (e.g., resin). For example, FIG. 1A shows bracket 102 mounted to tooth 100 via bonding material 106.

Figure 5A:
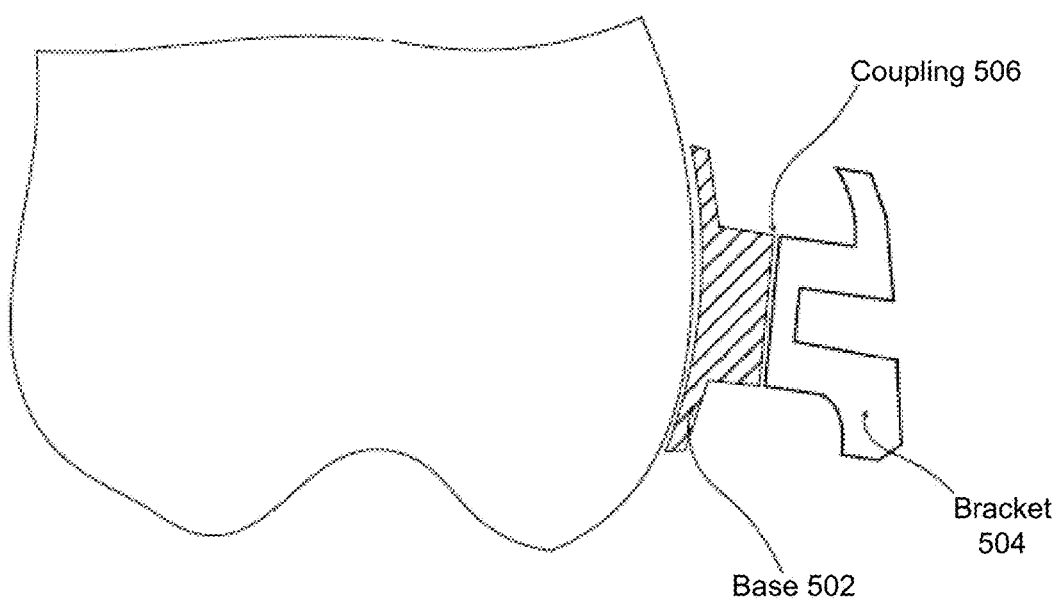
FIGS. 5A-5C show perspective views of representative brackets in accordance with some implementations.
Figure 5B:
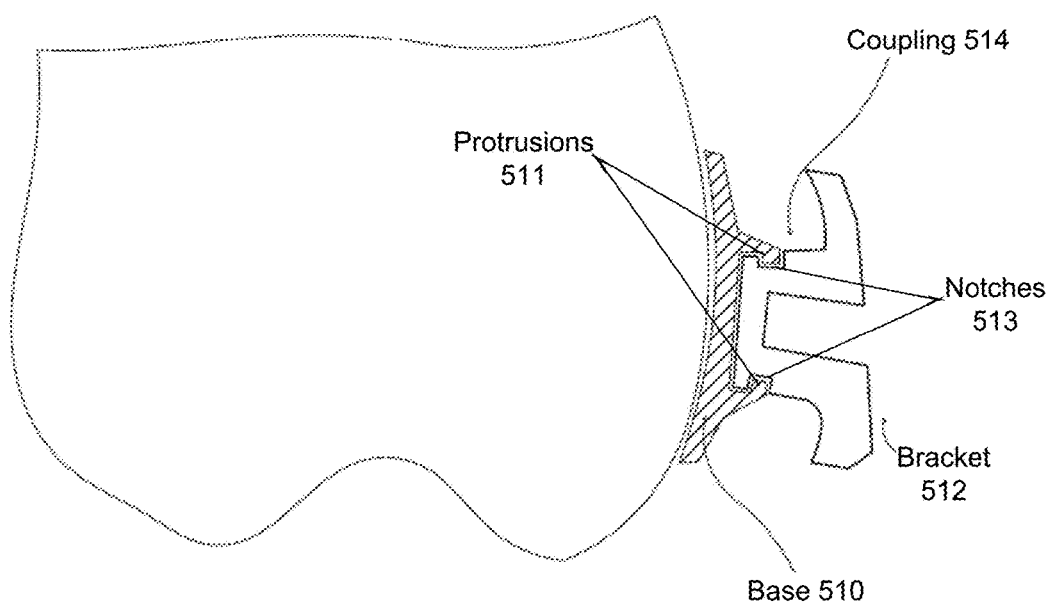
Figure 5C:
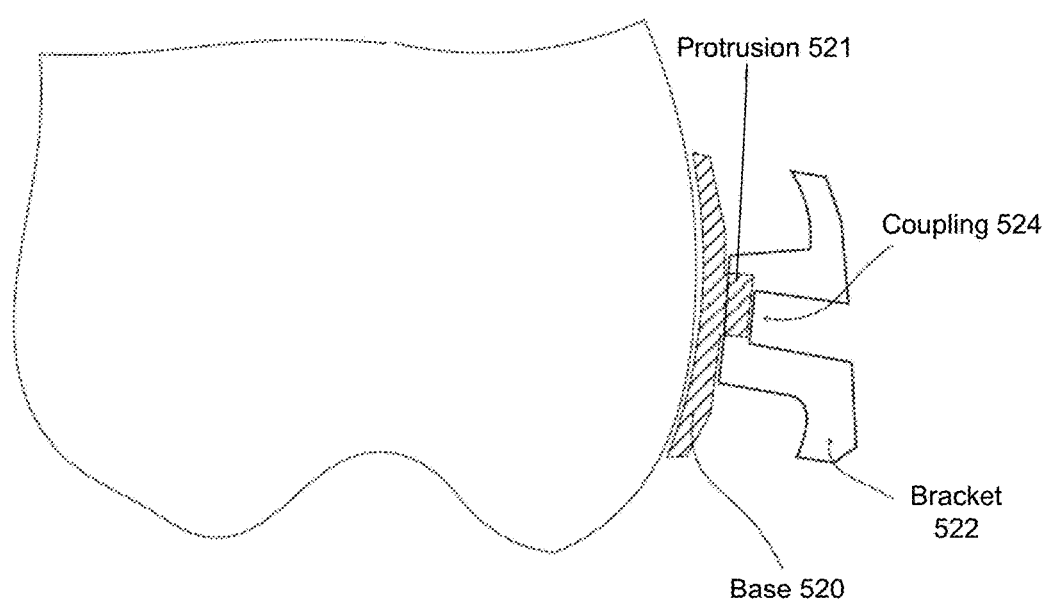

FIGS. 5A-5C show perspective views of representative brackets in accordance with some implementations. FIG. 5A shows a bracket 504 coupled to a base 502 via a coupling 506 in accordance with some implementations. In some implementations, the bracket 504 comprises a pre-manufactured bracket independent of an individual patient's prescription. In some implementations, the coupling 506 comprises a welded coupling (e.g., a laser-welded coupling). In some implementations, the base 502 comprises a custom base produced in accordance with a patient's prescription. In some implementations, the length and/or width of the base 502 is based on a shape of a corresponding tooth of the patient. In some implementations, the length and/or width of the base 502 is based on an alignment between the corresponding tooth and neighboring teeth of the patient. In some implementations, the length and/or width of the base 502 is based on an intended correction for the patient. In some implementations, the bracket 504 is configured to couple to the base 502 before the base is affixed to a patient's tooth. In some implementations, the bracket 504 is configured to couple to the base 502 prior to the base being affixed to a patient's tooth.

In some implementations, the base 502 is produced via a 3-D) printing. In some implementations, producing the base 502 includes generating a computer model of the base based on a patient's prescription. In some implementations, producing the base 502 includes generating a computer model of the base based measurements of a patient's teeth (e.g., based on a mold of the patient's teeth). In some implementations, producing the base 502 includes printing, via a 3-D printer, the computer model of the base.

In some implementations, the base 502 is comprised of a material distinct from a material of the bracket 504. In some implementations, the base 502 comprises resin, plastic, polymer, or the like. In some implementations, the base 502 comprises a metal base. In some implementations, the bracket 504 is comprised of metal, plastic, polymer, or the like.

FIG. 5B shows a bracket 512 coupled to a base 510 via a coupling 514 in accordance with some implementations. In some implementations, the bracket 512 comprises a pre-manufactured bracket independent of an individual patient's prescription. In some implementations, the base 510 comprises a custom base produced in accordance with a patient's prescription. In the example of FIG. 5B, the bracket 512 includes notches 513 and the base 510 includes corresponding protrusions 511 for aligning and/or affixing the bracket 512 to the base 510. In some implementations, the bracket 512 is affixed to the base 514 via a mechanical lock. In some implementations, the coupling 514 comprises a mechanical coupling (e.g., utilizing notches 513 and protrusions 511) and/or a welded coupling (e.g., a laser-welded coupling).

FIG. 5C shows a bracket 522 coupled to a base 520 via a coupling 524 in accordance with some implementations. In some implementations, the bracket 522 comprises a pre-manufactured bracket independent of an individual patient's prescription. In some implementations, the base 520 comprises a custom base produced in accordance with a patient's prescription. In the example of FIG. 5C, the bracket 522 includes a cavity and the base 520 includes corresponding protrusion 521 for aligning and/or affixing the bracket 522 to the base 520. In some implementations, the bracket 522 is affixed to the base 524 via a mechanical lock. In some implementations, the coupling 524 comprises a mechanical coupling (e.g., utilizing the cavity in the bracket 522 and the protrusion 521 in the base 520) and/or a welded coupling (e.g., a laser-welded coupling). In some implementations, the protrusion 521 comprises a distinct material from the material of the base 520. In some implementations, the protrusion 521 is utilized to align the bracket 522 with the base 520.

Figure 6A:
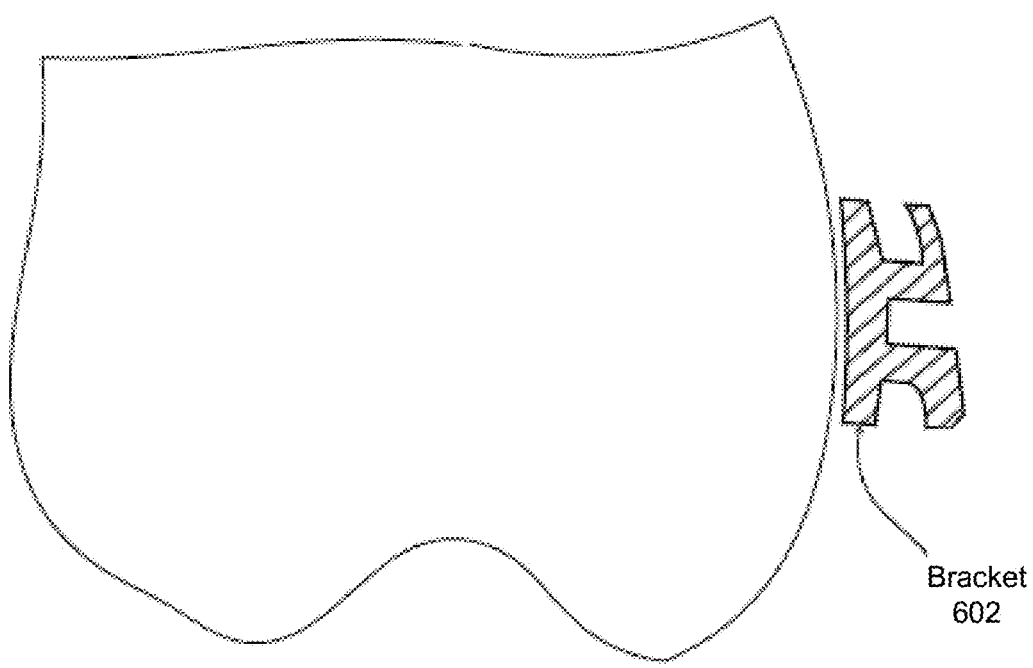
FIGS. 6A-6C show perspective views of representative brackets in accordance with some implementations.
Figure 6B:
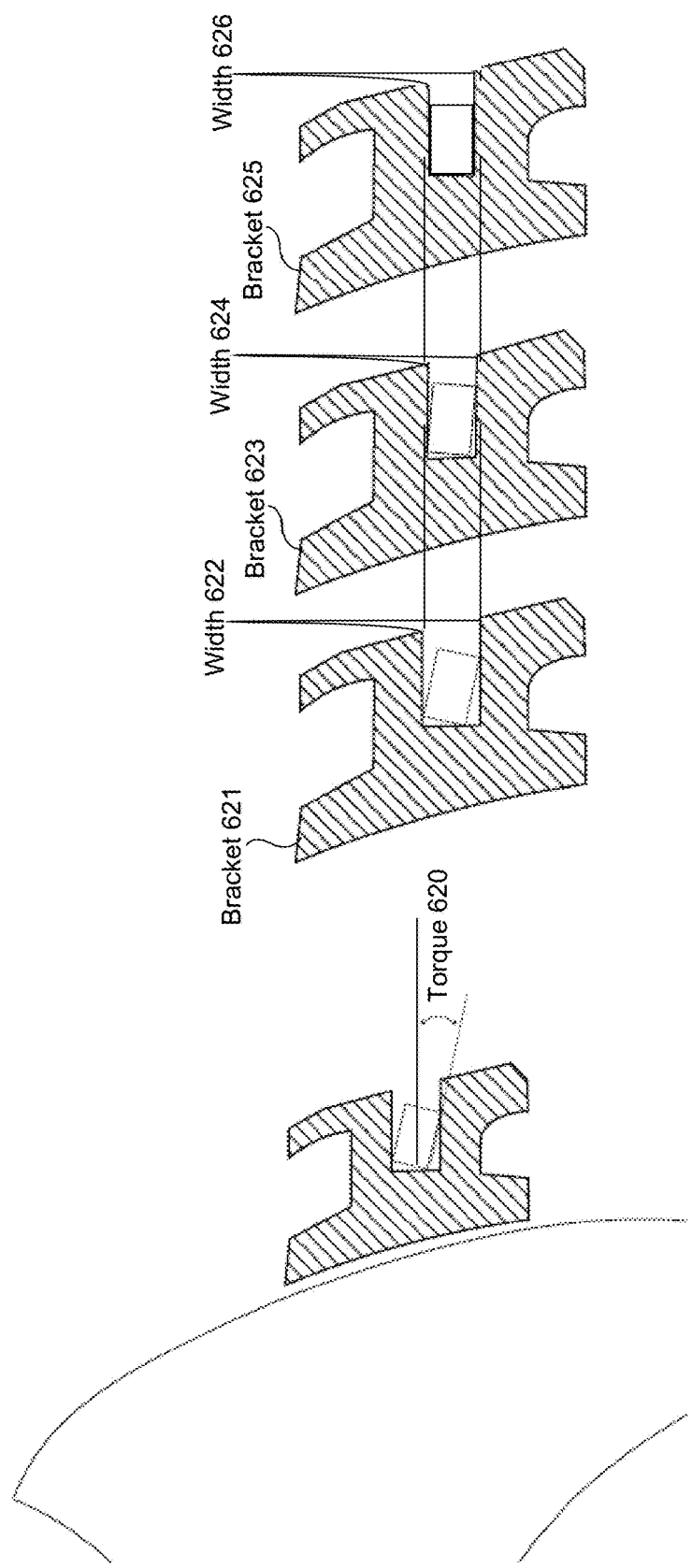
Figure 6C:
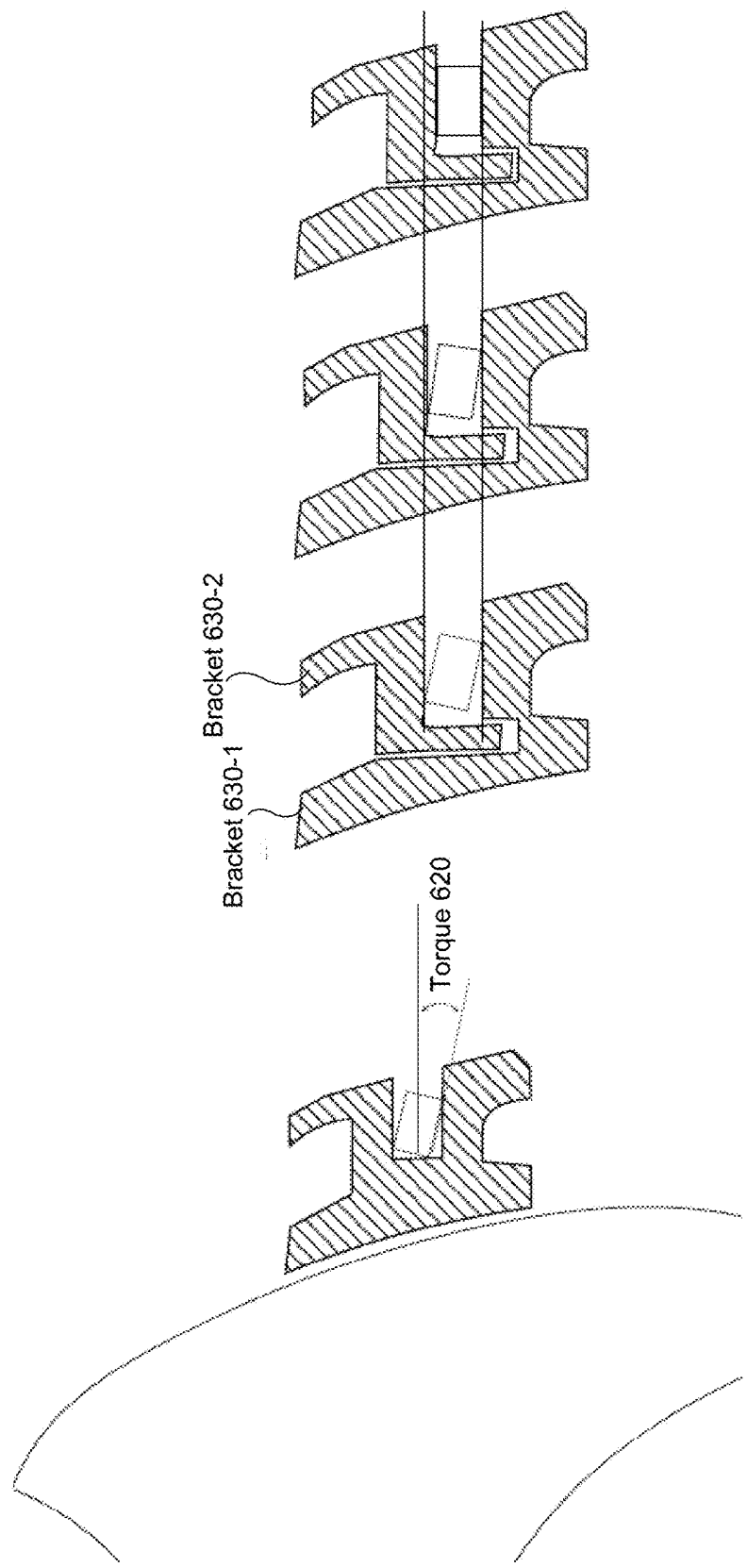

FIGS. 6A-6C show perspective views of representative brackets in accordance with some implementations. FIG. 6A shows a bracket 602. In some implementations, the bracket 602 comprises a custom bracket produced in accordance with a patient's prescription. In some implementations, the length and/or width of a base portion of the bracket 602 is based on a shape of a corresponding tooth of the patient. In some implementations, the length and/or width of a base portion of the bracket 602 is based on an alignment between the corresponding tooth and neighboring teeth of the patient. In some implementations, the length and/or width of a base portion of the bracket 602 is based on an intended correction for the patient.

In some implementations, the bracket 602 is produced via a 3-D printing. In some implementations, producing the bracket 602 includes generating a computer model of the bracket based on a patient's prescription. In some implementations, producing the bracket 602 includes generating a computer model of the bracket based measurements of a patient's teeth (e.g., based on a mold of the patient's teeth). In some implementations, producing the bracket 602 includes printing, via a 3-D printer, the computer model of the bracket.

FIG. 6B shows brackets 621, 623, and 625 having different widths 622, 624, and 626 respectively for the guide wire slot. The fit between the guide wire (also sometimes called an "archwire") and the guide wire slot affects how much of the torque 620 is lost. For example, bracket 621 has a large width 622 and thus loses more torque than bracket 623 or bracket 625. In some implementations, sizing of the guide wire slot (e.g., the width of the slot) is based on a patient's prescription (e.g., is based on how much torque is optimal for the particular tooth). In some implementations, sizing of the guide wire slot is based on a size and/or shape of the guide wire (e.g., a gauge of the wire). In some implementations, the width for the guide wire slot range from 0.019 inches to 0.022 inches. In some instances and implementations, a shifting angle of 9 degrees between the guide wire and the bracket corresponds to a baseline torque on the bracket, a shift angle of 17 degrees corresponds to 10 percent less torque, and a shift angle of 23 degrees corresponds to 20 percent less torque.

FIG. 6C shows a bracket 630 having two parts, 630-1 and 630-2, in accordance with some implementations. In some implementations, the parts 630-1 and 630-2 of the bracket 630 are coupled so as to optimize a width for the guide wire slot of the bracket 630. For example, the parts 630-1 and 630-2 are positioned such that a particular width is created for the guide wire slot, where the particular width is based on sizing of the guide wire and/or the patient's prescription. In some implementations, the two parts are coupled via a bonding material (e.g., a resin). In some implementations, the two parts are coupled via a welding (e.g., a laser welding). In some implementations, the two parts 630-1 and 630-2 are positioned to optimize a width for the guide wire slot and then coupled (e.g., via a bonding material or welding).

Figure 7A:
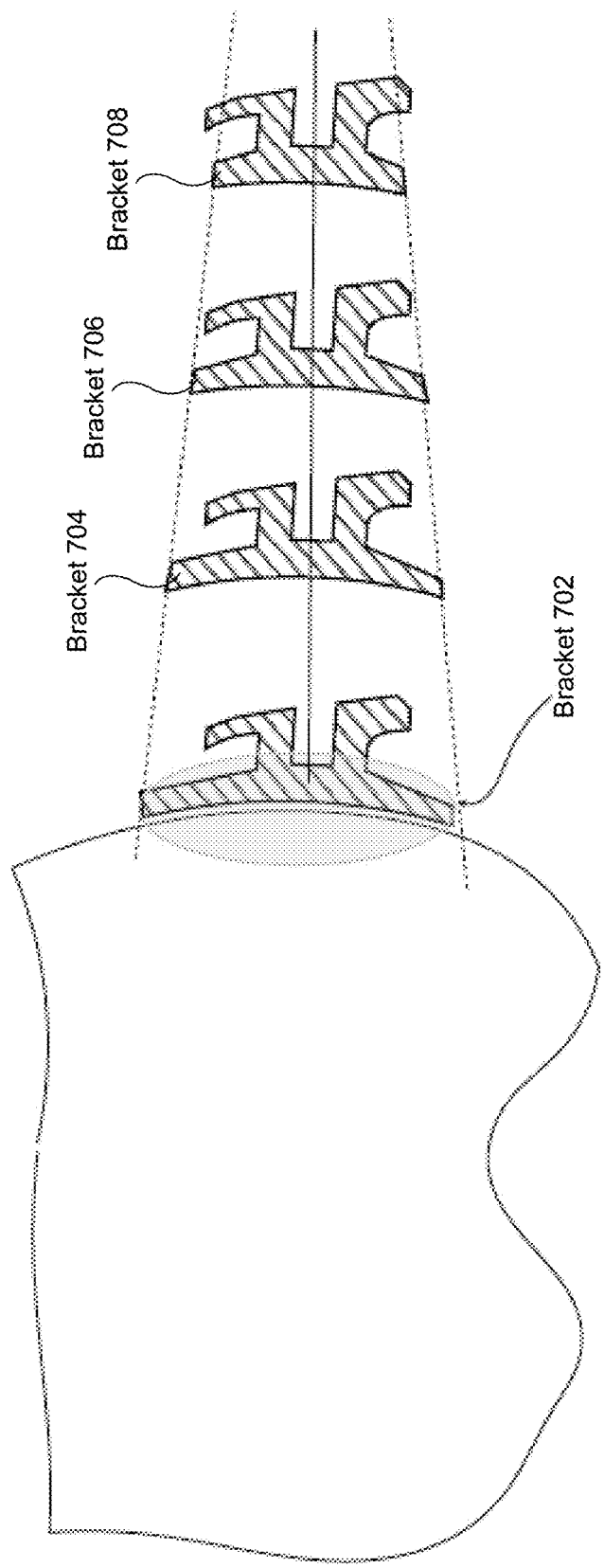
FIGS. 7A-7E show perspective views of representative brackets in accordance with some implementations.

FIGS. 7A-7E show perspective views of representative brackets in accordance with some implementations. FIG. 7A shows brackets 702, 704, 706, and 708 with differing sized bases (e.g., bracket 702 has the largest base and bracket 708 has the smallest base). In some implementations, the base size of the bracket is based on a patient's tooth size and/or prescription. Larger base size enhances bonding between the bracket and the tooth to prevent dislodging of the bracket. Smaller base size increases aesthetics and minimizes the orthodontic footprint for the patient. In some implementations, producing a bracket with a base size based on a patient's tooth and/or prescription includes generating a computer model of the bracket based on a mapping of the patient's teeth. In some implementations, producing the bracket includes printing, via a 3-D printer, the computer model of the bracket.

Figure 7C:
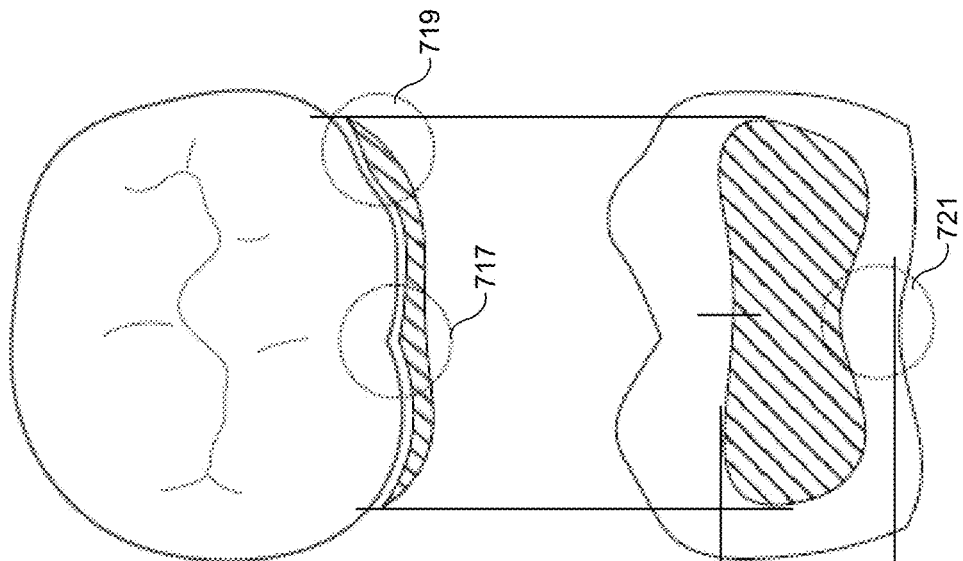
Figure 7B:
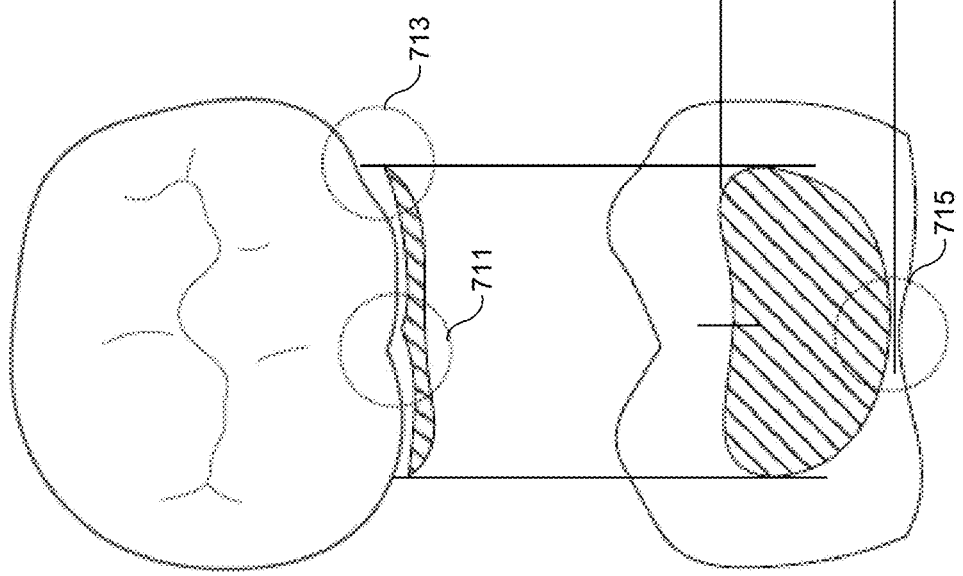

FIG. 7B illustrates misfit between a pre-fabricated bracket and a patient's tooth. FIG. 7B shows a first misalignment at 711 and a second misalignment at 713 (e.g., due to the bracket not having been fabricated in accordance with the patient's teeth and/or prescription). Due to misalignment the bracket in FIG. 7B is easier to dislodge (e.g., than the bracket in FIG. 7C). FIG. 7B also shows the bracket in close proximity to the patient's gingiva at 715. The close proximity of the bracket may lead to more inflammation and discomfort for the patient. The close proximity of the bracket may also make cleaning of the tooth, bracket, and/or gingiva more difficult.

FIG. 7C illustrates how the issues in FIG. 7B are alleviated by use of a custom bracket (e.g., based on a patient's particular tooth). In areas 717 and 719 the custom bracket fits more closely with the patient's tooth (e.g., compared to the bracket in FIG. 7B) enhancing bonding between the bracket and the tooth and decreasing the likelihood of the bracket becoming dislodged during use. In area 721 there is a larger spacing between the bracket and the patient's gingiva (e.g., compared to the bracket in FIG. 7B) decreasing the likelihood of inflammation and discomfort for the patient. In some implementations, the custom bracket is produced based on the shape of the patient's tooth and/or the patient's prescription so as to optimize bonding between the bracket and the tooth and to minimize discomfort for the patient.

Figures 7D, 7E:
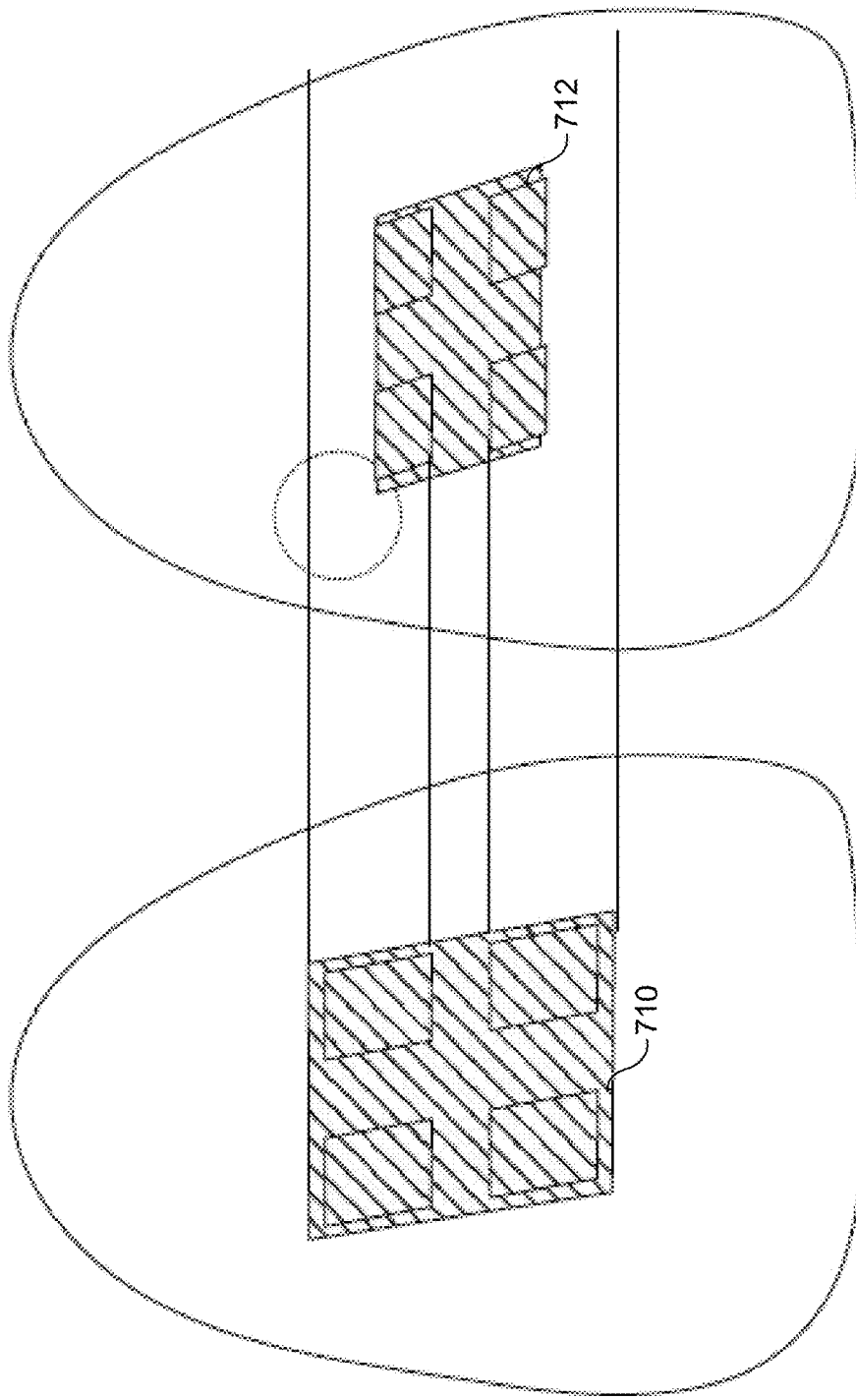

FIG. 7D shows a pre-fabricated bracket 710 bonded to the patient's tooth. The bracket 710 in FIG. 7D is fabricated independent of the patient's tooth. Conversely, the bracket 712 in FIG. 7E is produced based on the size and/or shape of the patient's tooth. The bracket 712 is produced to optimize spacing between the bracket and the patient's gingiva in accordance with some implementations. The sizing of bracket 712 is also optimized based on the patient's prescription (e.g., based on an amount of force and/or torque to be applied to align the patient's teeth) in accordance with some implementations.

Figure 8A:
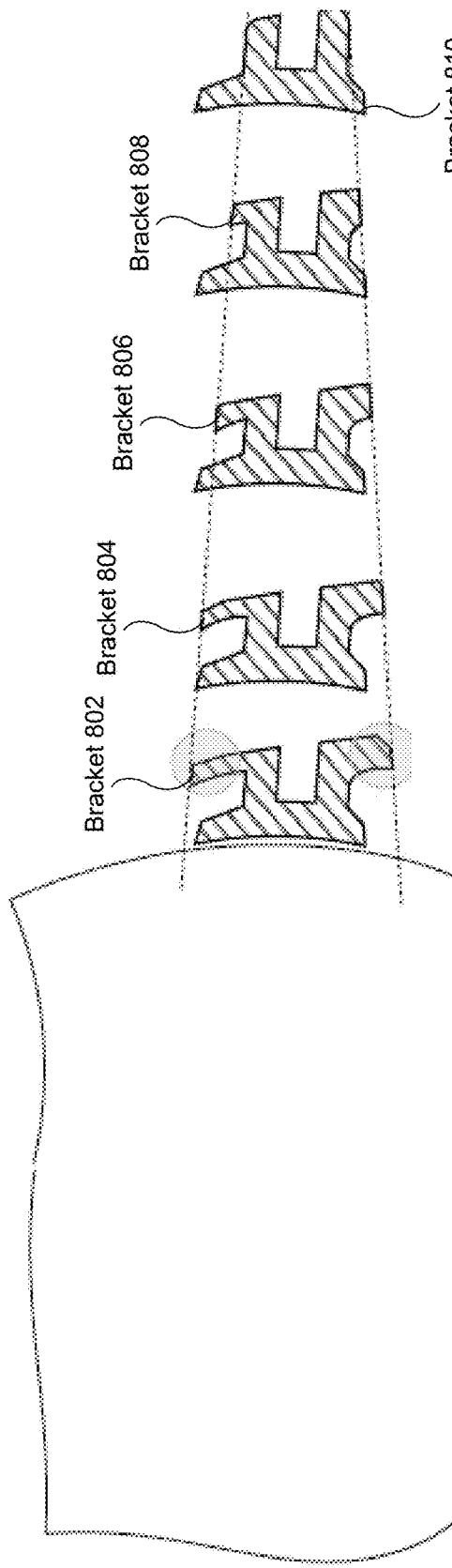
FIGS. 8A-8C show perspective views of representative brackets in accordance with some implementations.
Figure 8C:
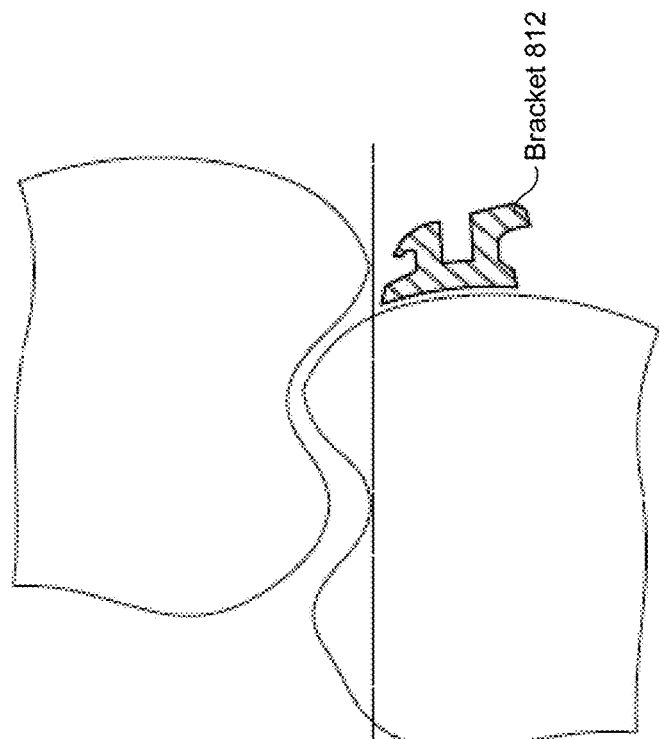
Figure 8B:
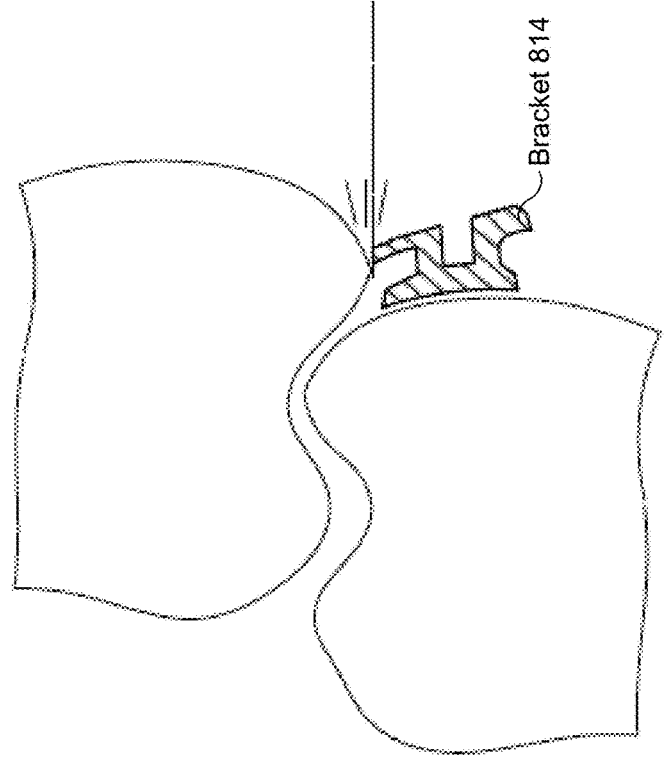

FIGS. 8A-8C show perspective views of representative brackets in accordance with some implementations. FIG. 8A shows brackets 802, 804, 806, 808, and 810 having different wing sizes. For example, the bracket 802 has the largest wing size, the bracket 808 has the smallest wing size, and the bracket 810 has no wings. In some implementations, the wing size of the bracket is optimized for a particular patient (e.g., is based on the patient's prescription). The wing size of the bracket is minimized to increase patient comfort (e.g., minimize chance of the patient developing ulcers), improve oral hygiene (e.g., by minimizing trapping of food and easing cleaning of the bracket and/or tooth), and/or improve aesthetics in accordance with some implementations. In some implementations, bracket wings are used to attach elastic bands for coupling the bracket to another bracket in the patient's mouth. In some implementations, a bracket is produced with bracket wings in accordance with a determination that the patient's prescription requires an elastic band attached to the bracket. In some implementations, a bracket is produced without bracket wings in accordance with a determination that the patient's prescription does not require an elastic band to be attached to the bracket.

In some implementations, the bracket wing parameters (e.g., angle, size, shape, etc.) are based at least in part on the patient's bite. For example, the custom bracket 812 in FIG. 8C is produced to avoid interfering with the patient's bite and/or minimize dislodging of the bracket due to the patient's bite. Conversely, the pre-fabricated bracket 814 in FIG. 8B interferes with the patient's bite.

FIGS. 9A-9C show representative brackets customized in accordance with a patient's preferences. For example, FIG. 9A shows a bracket 902 with gold plating. In some implementations, the patient is enabled to select a plating or coating for the bracket. For example, a patient can select from a list of color options, including one or more patterns and/or one or more images. In some implementations, the bracket is produced in accordance with a custom coating or plating received from, or generated in accordance with input from, the patient. FIG. 9B shows a bracket 904 with a star-shape and FIG. 9C shows a bracket 906 with a heart shape. In some implementations, the star-shape is one of a list of shape options for selection by a patient. For example, a patient selects from defined shapes such as heart-shaped, star-shaped, diamond-shaped, etc. In some implementations, the bracket is produced with a custom shape generated in accordance with the patient's preferences. In some implementations, the patient is enabled to select one or more accessories, such as a diamond or crystal, for the bracket. In some implementations, the selected accessory is affixed to the bracket.

In some implementations, a bracket is produced in accordance with a patient's prescription and in accordance with one or more aesthetic preferences of the patient. In some implementations, producing the bracket in accordance with the one or more aesthetic preferences of the patient includes: (1) displaying to the patient a list of aesthetic design options; and (2) receiving selection of one or more of the aesthetic options from the patient. In some implementations, the displayed list of aesthetic design options is based at least in part on the patient's prescription. For example, in accordance with a determination that a patient's prescription requires that the bracket have large bracket wings (e.g., bracket 802 in FIG. 8A), the displayed list of aesthetic design options includes only aesthetic design options for brackets with large bracket wings.

In some implementations, a bracket is composed of a particular material selected based on a patient's prescription and/or the patient's aesthetic preferences. For example, a bracket is optionally produced with either a harder alloy or a softer alloy based on a patient's prescription. As another example, a bracket is composed of a gold or platinum alloy in accordance with a patient's aesthetic preference.

It will also be understood that, although the terms first, second, etc. are, in some instances, used herein to describe various elements, these elements should not be limited by these terms. These terms are only used to distinguish one element from another. For example, a first bracket could be termed a second bracket, and, similarly, a second bracket could be termed a first bracket, without departing from the scope of the various described implementations. The first bracket and the second bracket are both brackets, but they are not the same bracket.

The terminology used in the description of the various described implementations herein is for the purpose of describing particular implementations only and is not intended to be limiting. As used in the description of the various described implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software or any combination thereof.

The foregoing description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

What is claimed is:

1. A method for applying a set of orthodontic brackets to a set of teeth of a patient, comprising:
   for each tooth in the set of teeth, determining an optimal orientation for a respective orthodontic bracket in the set of orthodontic brackets to be mounted to the tooth;
   producing a flexible bracket applicator having a squeeze handle and configured to mount each orthodontic bracket in the set of orthodontic brackets to the respective tooth in the set of teeth in the respective optimal orientation via application of an elastic force to the set of teeth; and
   mounting the set of orthodontic brackets to the set of teeth using the bracket applicator and a bonding material, including:
      increasing a radius of the bracket applicator for insertion in the patient's mouth by squeezing the squeeze handle; and
      reducing the radius of the bracket applicator to apply the elastic force to the set of teeth by ceasing to squeeze the squeeze handle.

2. The method of claim 1, wherein determining the optimal orientation comprises determining an optimal tip, torque, and rotation for the respective orthodontic bracket.

3. The method of claim 1, wherein determining the optimal orientation comprises utilizing a 3-dimensional model of the set of teeth to determine the optimal orientation.

4. The method of claim 1, wherein the respective optimal orientation for a first orthodontic bracket is distinct from the respective optimal orientation for a second orthodontic bracket.

5. The method of claim 1, wherein the bracket applicator is configured to utilize one or more respective tooth surfaces to position each orthodontic bracket at the respective optimal orientation.

6. The method of claim 1, further comprising producing a mold of the set of teeth of the patient; and
   wherein producing the flexible bracket applicator comprises producing the flexible bracket applicator based on the mold and the respective optimal orientations.

7. The method of claim 1, wherein the flexible bracket applicator comprises a plurality of tooth mounts and a flexible connector coupling the plurality of tooth mounts to one another.

8. The method of claim 1, wherein the squeeze handle is configured to enable the bracket applicator to selectively engage the set of teeth.

9. A bracket applicator, comprising:
   a squeeze handle configured to selectively engage the bracket applicator with a patient's teeth, wherein the squeeze handle is adapted such that:
      squeezing the squeeze handle increases a radius of the bracket applicator for insertion in the patient's mouth; and
      ceasing to squeeze the squeeze handle reduces the radius of the bracket applicator to apply an elastic force to the patient's teeth;
   a bracket mount configured to secure an orthodontic bracket; and
   a tooth mount coupled to the bracket mount, the tooth mount configured to mount the orthodontic bracket to a tooth in a particular orientation.

10. The bracket applicator of claim 9, further comprising:
    a plurality of additional bracket mounts each configured to secure a respective orthodontic bracket;
    a plurality of additional tooth mounts coupled to the plurality of additional bracket mounts; and
    a flexible connector coupling the tooth mount to each tooth mount in the plurality of additional tooth mounts, the flexible connector configured to enable concurrent mounting of each orthodontic bracket at a respective particular orientation.

11. The bracket applicator of claim 10, wherein the squeeze handle is further configured to enable the bracket applicator to selectively engage a posterior undercut during mounting.

12. The bracket applicator of claim 10, wherein the flexible connector comprises a plurality of connecting sections, each connecting section of the plurality of connecting sections coupling two adjacent tooth mounts; and wherein at least one connecting section of the plurality of connecting sections is distinct from at least one other connecting section of the plurality of connecting sections.

13. The bracket applicator of claim 10 wherein the flexible connector is coupled to the tooth mount and each tooth mount of the plurality of additional tooth mounts via a respective connector fastener.

14. The bracket applicator of claim 10, wherein the flexible connector comprises an anterior connector; and the bracket applicator further comprises a posterior connector coupling the tooth mount to each tooth mount in the plurality of additional tooth mounts;

wherein the posterior connector is more rigid than the anterior connector.

15. The bracket applicator of claim 10, wherein the tooth mounts are adapted to align respective bracket mounts to corresponding tooth surfaces of the patient's teeth.

16. The bracket applicator of claim 9, wherein the bracket mount is further configured to enable removal of excess bonding material during mounting of the orthodontic bracket.

17. The bracket applicator of claim 9, wherein the bracket mount is further configured to minimize bonding of the bracket mount to a tooth.

18. The bracket applicator of claim 9, wherein the bracket mount is further configured to selectively release the orthodontic bracket without weakening a bond between the orthodontic bracket and a tooth.

* * * * *